United States Patent
Tamada et al.

(10) Patent No.: US 11,337,997 B2
(45) Date of Patent: May 24, 2022

(54) IMMUNOCOMPETENT CELL AND EXPRESSION VECTOR EXPRESSING REGULATORY FACTORS OF IMMUNE FUNCTION

(71) Applicant: YAMAGUCHI UNIVERSITY, Yamaguchi (JP)

(72) Inventors: Koji Tamada, Yamaguchi (JP); Yukimi Sakoda, Yamaguchi (JP); Keishi Adachi, Yamaguchi (JP)

(73) Assignee: Yamaguchi University, Yamaguchi (JP)

( * ) Notice: Subject to any disclaimer, the term of this patent is extended or adjusted under 35 U.S.C. 154(b) by 681 days.

(21) Appl. No.: 16/084,503

(22) PCT Filed: Mar. 15, 2017

(86) PCT No.: PCT/JP2017/010437
§ 371 (c)(1),
(2) Date: Sep. 12, 2018

(87) PCT Pub. No.: WO2017/159736
PCT Pub. Date: Sep. 21, 2017

(65) Prior Publication Data
US 2019/0099446 A1    Apr. 4, 2019

(30) Foreign Application Priority Data

Mar. 17, 2016   (JP) .............................. JP2016-053913

(51) Int. Cl.
| | |
|---|---|
| *A61K 35/17* | (2015.01) |
| *C12N 5/10* | (2006.01) |
| *C12N 15/09* | (2006.01) |
| *A61K 39/00* | (2006.01) |
| *C07K 14/54* | (2006.01) |
| *C07K 14/725* | (2006.01) |
| *C12N 5/0783* | (2010.01) |
| *C12N 15/79* | (2006.01) |

(52) U.S. Cl.
CPC .......... *A61K 35/17* (2013.01); *A61K 39/0011* (2013.01); *C07K 14/5418* (2013.01); *C07K 14/7051* (2013.01); *C12N 5/0636* (2013.01); *C12N 5/10* (2013.01); *C12N 15/09* (2013.01); *C12N 15/79* (2013.01)

(58) Field of Classification Search
CPC ................ A61K 35/17; A61K 39/0011; A61K 2039/5158; C07K 14/5418; C07K 14/7051; C12N 5/10; C12N 2510/00; C12N 5/0636
See application file for complete search history.

(56) References Cited

U.S. PATENT DOCUMENTS

2013/0287748 A1    10/2013 June et al.
2013/0287752 A1    10/2013 Davila et al.
2013/0288368 A1    10/2013 June et al.
2014/0255363 A1*   9/2014 Metelitsa ............... A61K 45/06
                                                   424/93.21
2017/0291953 A1    10/2017 Tamada et al.

FOREIGN PATENT DOCUMENTS

| EP | 3205720 | 8/2017 |
| JP | 2013-116891 A | 6/2013 |
| JP | 2014-504294 A | 2/2014 |
| JP | 2014-507118 A | 3/2014 |
| WO | WO 2011/119773 | 9/2011 |
| WO | WO 2013/123061 A1 | 8/2013 |
| WO | WO 2016/056228 A1 | 4/2016 |

OTHER PUBLICATIONS

Siegert and Luther. Frontiers in Immunology, 2012, vol. 3, article 285, pp. 1-10 (Year: 2012).*
Yozo Nakazawa, "Gene-modified T-cell Therapy Using Chimeric Antigen Receptor", The Shinshu Medical Journal, Aug. 2013, vol. 61, No. 4, pp. 197-203, 199-201 (partial translation included).
Sato-Hashimoto M. et al., J. Immunol., 2011, vol. 187, No. 1, 291-7.
Siegert S. et al., Front. Immunol., 2012, vol. 3, article 285.
Yukimi Satoda, Koji Tamada "CAR-T Saibo Ryoho no Kaihatsu to Saishin Kenkyu no Doko", Molecular Targeted Therapy for Cancer, Jul. 24, 2015 (Jul. 24, 2015), vol. 13, No. 2, pp. 90-98, 91-96 (English summary and partial translation attached).
Koji Tamada, "Adoptive immunotherapy against cancer using CAR-expressing T cells", Journal of Clinical and Experimental Medicine, Feb. 13, 2016 (Feb. 13, 2016), vo. 256, No. 7, pp. 805-809, 806-809 (partial translation attached).
Miho Hashimoto (Sato) et al., "Hizo T-saibo no Kojosei Chosetsu eno SIRPα no Kan'yo", Dai 85 Kai Annual Meeting of Japanese Biochemical Society Yoshishu, 2012, 3T29-06 (substitute for the English translation).
Markley et al., "IL-7 and IL-21 are superior to IL-2 and IL-15 in promoting human T cell-mediated rejection of systemic lymphoma in immunodeficient mice," Blood 115 (17): 3508-3519 (2010).
Cardell et al., "Combined CCL 19/IL-7 treatment eradicates tumors in murine models of lung cancer," Journal of Thoracic Oncology, 2 (8) Supplement 4, P3-020 (2007).

* cited by examiner

*Primary Examiner* — Antonio Galisteo Gonzalez
*Assistant Examiner* — Khaleda B Hasan
(74) *Attorney, Agent, or Firm* — Morgan, Lewis & Bockius LLP

(57) ABSTRACT

It is to provide an immunocompetent cell that expresses regulatory factors of immunocompetent cell immune function and possesses all of proliferative potential, viability, and the ability to accumulate a T cell, and an expression vector of regulatory factors of immune function for generating the immunocompetent cell. An immunocompetent cell expressing a cell surface molecule specifically recognizing a cancer antigen, interleukin 7 (IL-7), and CCL19 is generated. Preferably, the cell surface molecule specifically recognizing a cancer antigen is T cell receptor specifically recognizing the cancer antigen, and the immunocompetent cell is a T cell.

19 Claims, 5 Drawing Sheets
Specification includes a Sequence Listing.

[Figure 1]
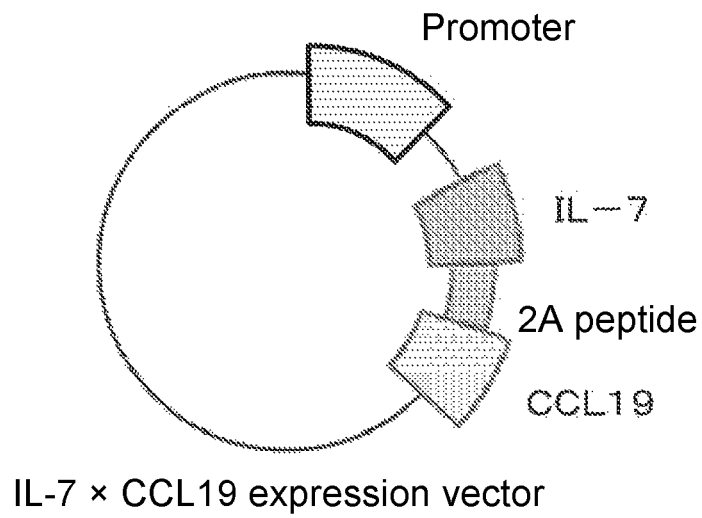
IL-7 × CCL19 expression vector
[Figure 2A]
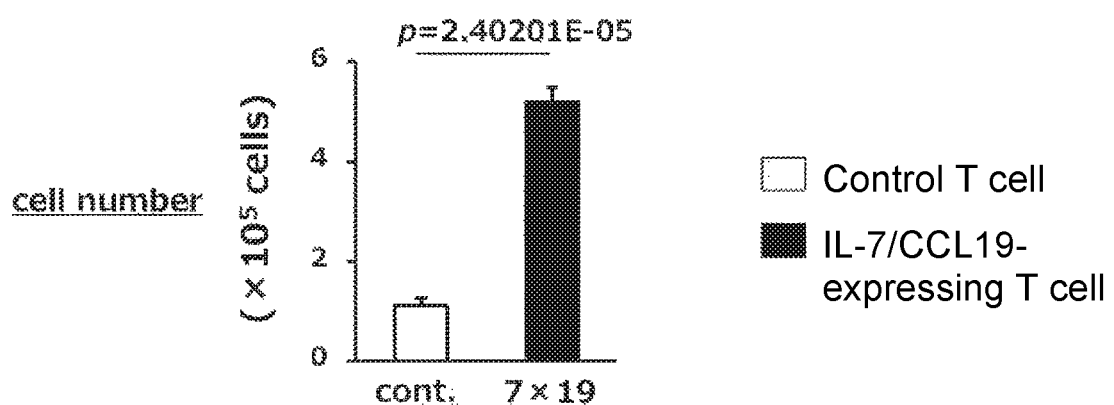

[Figure 2B]
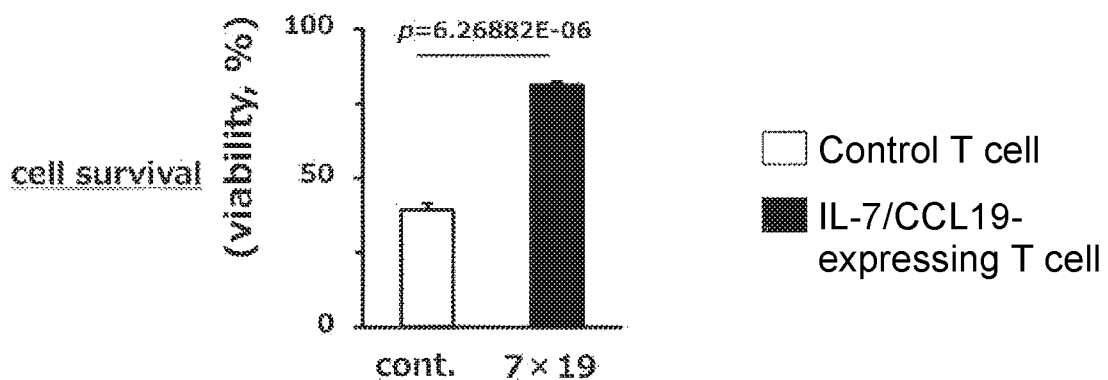
[Figure 3]
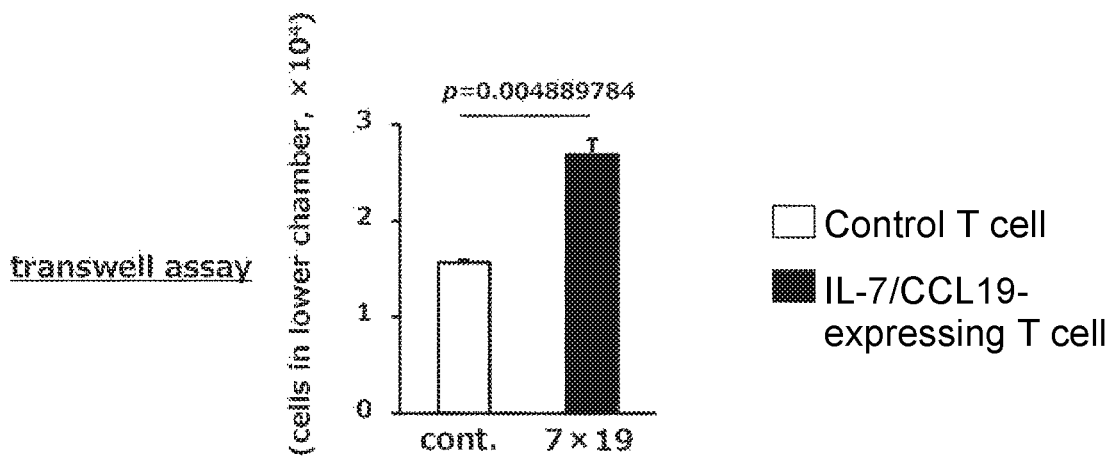

[Figure 4]
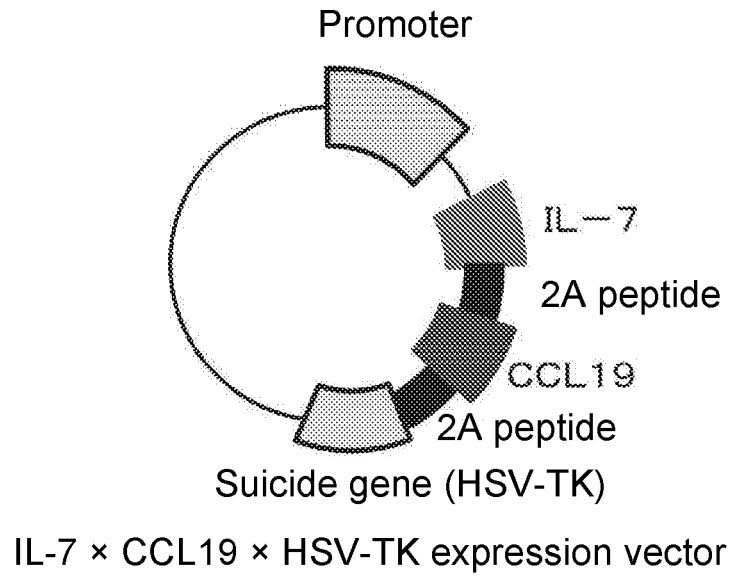
IL-7 × CCL19 × HSV-TK expression vector
[Figure 5]
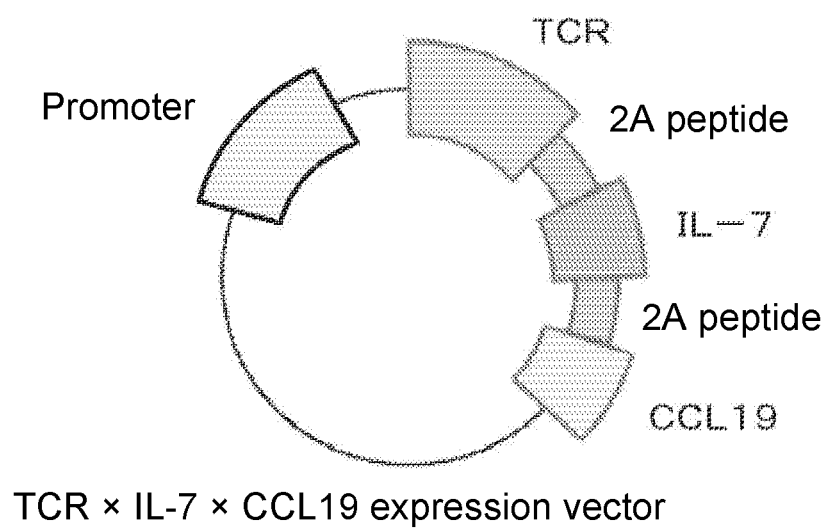
TCR × IL-7 × CCL19 expression vector

[Figure 6]
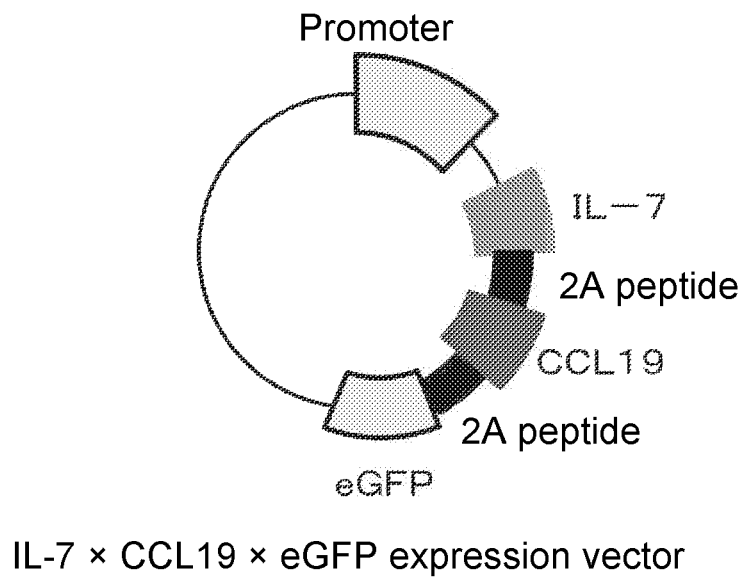
IL-7 × CCL19 × eGFP expression vector
[Figure 7]
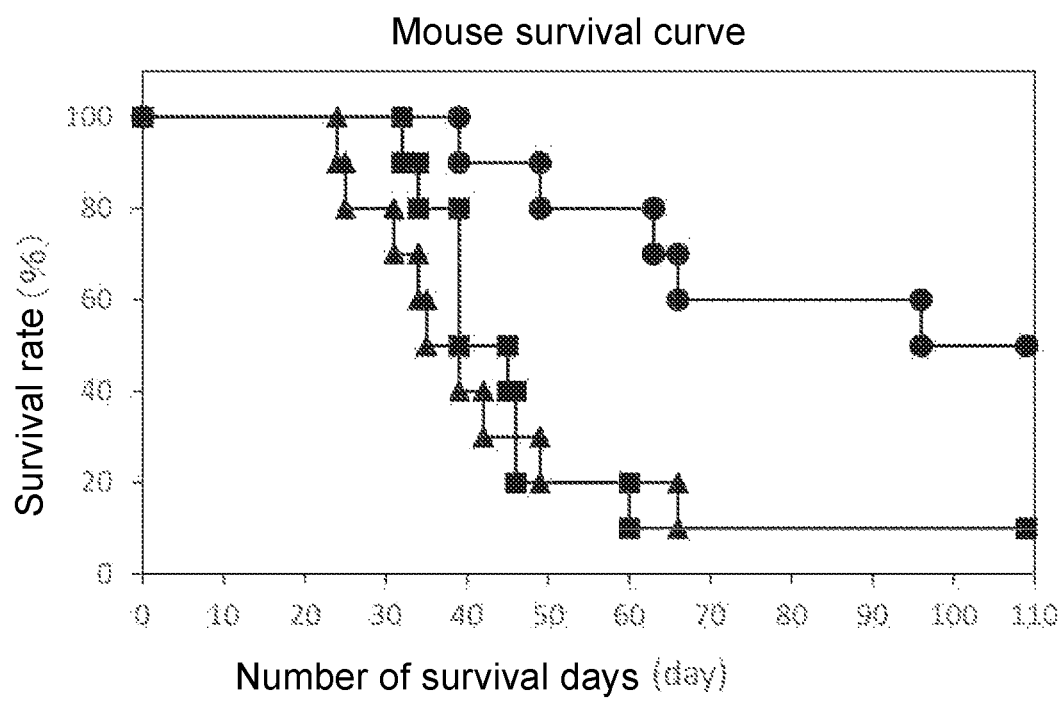

[Figure 8]
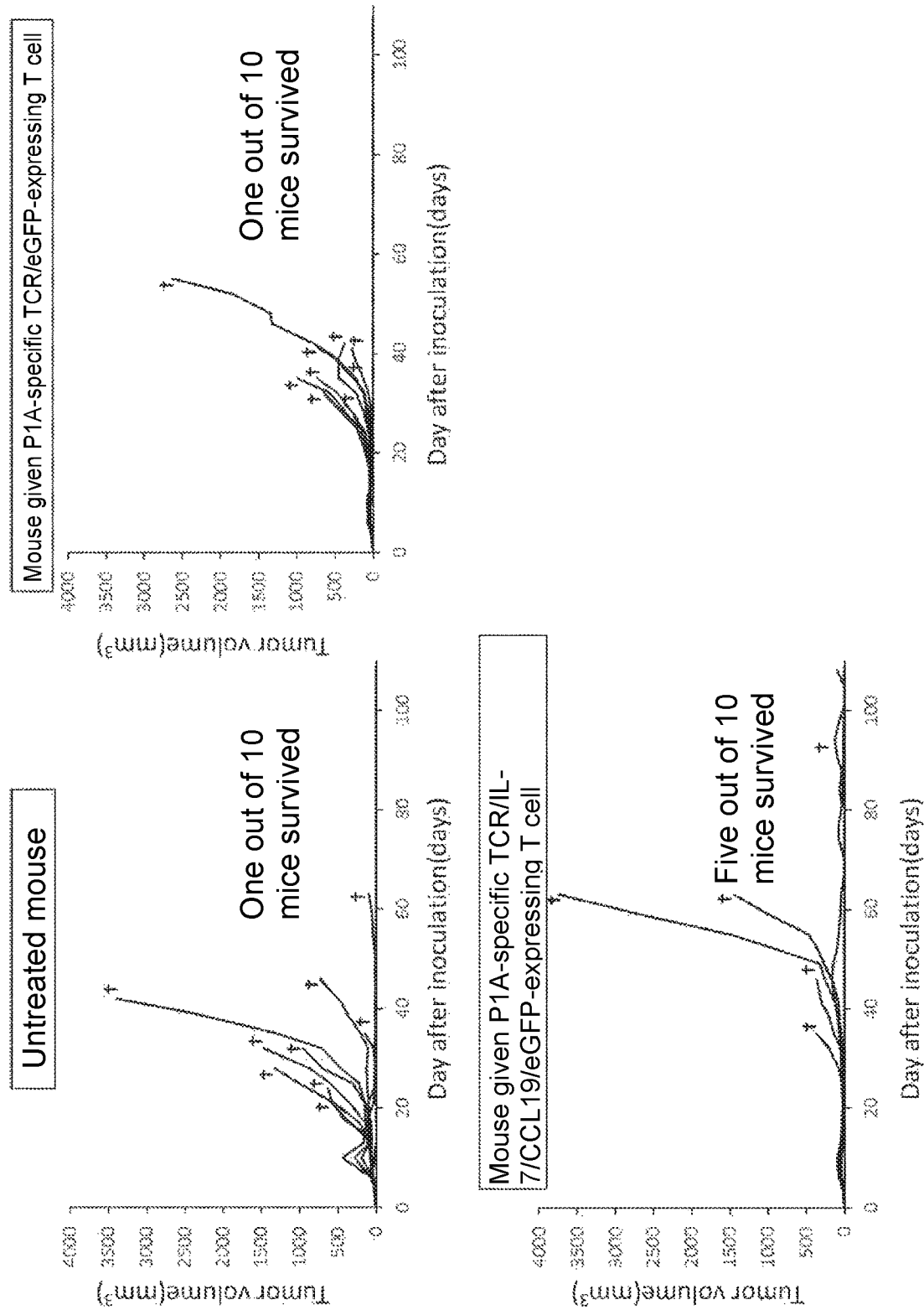

IMMUNOCOMPETENT CELL AND EXPRESSION VECTOR EXPRESSING REGULATORY FACTORS OF IMMUNE FUNCTION

TECHNICAL FIELD

The present invention relates to an immunocompetent cell expressing a cell surface molecule specifically recognizing a cancer antigen, interleukin 7 (IL-7), and CCL19, an anticancer agent containing the immunocompetent cell, and an expression vector for generating the immunocompetent cell.

BACKGROUND ART

Cancer is a disease that affects many people around the world. In general, chemotherapy, radiotherapy, or surgical therapy is widely practiced. However, there have been various problems in such a way that adverse reactions occur; some functions are lost; and metastasis is difficult to treat.

Accordingly, immunotherapy has been under development in recent years in order to keep patients' QOL higher. In this immunotherapy, immuno-cell therapy is therapy which involves collecting immunocompetent cells from patients, treating and amplifying the immunocompetent cells so as to enhance their immune function, and transferring the immunocompetent cells again to the patients. Specifically, therapy is known which involves collecting T cells from patients, introducing a gene encoding CAR to the T cells, amplifying the T cells, and transferring the T cells again to the patients (see non-patent document 1). This therapy is currently under clinical trial around the world and has yielded results that indicate effectiveness for, for example, malignant tumor in the hematopoietic organ, such as leukemia or lymphoma.

At least several hundred different types of factors such as cytokines, chemokines, and signal regulatory proteins are known as regulatory factors of immune function of immunocompetent cells such as T cells. Among them, interleukin 7 (IL-7) is a cytokine essential for the survival of T cells and is known to be produced by non-hematopoietic cells such as stromal cells of the bone marrow, the thymus, and lymphatic organs or tissues. A T cell expressing a chimeric cytokine receptor comprising IL-7 and IL-7R alpha fused with each other (see patent document 1) is disclosed as a T cell exploiting the function of this IL-7. However, the chimeric cytokine receptor in the T cell is expressed as one fusion protein in a manner limited to the membrane surface of the T cell introduced therewith, and merely transduces a signal of a cytokine such as IL-7R in a ligand-independent manner only to the autologous cell. Thus, the chimeric cytokine receptor cannot enhance the function of a T cell unintroduced with the receptor.

It is disclosed that: decreased expression of CCL19, CCL21, and IL-7 is responsible for deficiency in the maintenance of a T cell zone in the spleen of an SIRP alpha mutant mouse (see non-patent document 2); and CCL19, CCL21, and IL-7 work to maintain the homeostasis of T cells in secondary lymphoid tissues (spleen tissues or lymph nodes) (see non-patent document 3). However, non-patent documents 2 and 3 described above show an effect on nonactivated T cells constantly present in the T cell zones of secondary lymphoid tissues and do not show the direct relationship with antitumor immune response. Furthermore, CCL19-, CCL21-, or IL-7-expressing cells described in non-patent documents 2 and 3 were not T cells but were reticuloendothelial cells present in the secondary lymphoid tissues.

Meanwhile, T cell receptor (hereinafter, also referred to as "TCR") is an antigen receptor molecule expressed on the cell membranes of T cells. TCR is present as a heterodimer consisting of an alpha chain and a beta chain, or of a gamma chain and a delta chain and is known to activate T cells by recognizing an antigen molecule bound with a major histocompatibility complex (MHC) molecule.

Immunotherapy which involves introducing a gene of TCR capable of recognizing a tumor antigen expressed on cancer cells to T cells obtained from cancer patients, amplifying the T cells, and then transferring the T cells again to the patients is under development by the application of the function of this TCR. Specifically, a pharmaceutical composition for meningioma treatment containing a cell expressing TCR specifically recognizing a WT1-expressing cell (see patent document 2) is disclosed.

Although some of the techniques described above exhibit an antitumor effect on malignant tumor in the hematopoietic organ, none of the previous cases still exhibit a marked effect on solid cancer. This is considered to be due to the problems of low survival efficiency of transferred immunocompetent cells in vivo or insufficient activation of endogenous immunocompetent cells induced by transferred immunocompetent cells or insufficient local accumulation thereof to tumor. Thus, the development of a technique of solving these problems has been desired.

PRIOR ART DOCUMENTS

Patent Documents

Patent Document 1: International Publication No. WO 2013/123061
Patent Document 2: Japanese unexamined Patent Application Publication No. 2013-116891

Non-Patent Documents

Non-patent Document 1: Yozo Nakazawa, The Shinshu Medical Journal, 61 (4): 197-203 (2013)
Non-patent Document 2: SATO-HASHIMOTO M. et al., J. Immunol., 2011, vol. 187, no. 1, 291-7 Non-patent Document 3: SIEGERT S. et al., Front. Immunol., 2012, vol. 3, article 285

SUMMARY OF THE INVENTION

Object to be Solved by the Invention

Immunocompetent cells for use in conventional immunotherapy do not sufficiently potentiate the immunity-inducing effect of endogenous immunocompetent cells or the proliferative potential, survival capacity, or the ability of immunocompetent cells to accumulate a T cell. Accordingly, an object of the present invention is to provide an immunocompetent cell that expresses regulatory factors of immunocompetent cell immune function and possesses all of proliferative potential, survival capacity, and the ability to accumulate a T cell, and an expression vector of regulatory factors of immune function for generating the immunocompetent cell.

Means to Solve the Object

The inventors have attempted to improve cells expressing regulatory factors of immune function for the purpose of achieving a much better immunity-inducing effect or antitumor activity in cancer immunotherapy using immunocompetent cells. During the course thereof, the inventors have focused on cytokines, chemokines, and signal regulatory proteins which are factors regulating the immune function of immunocompetent cells, and constructed a vector for the expression of the factors regulating the immune function of immunocompetent cells. As a result of introducing this expression vector to immunocompetent cells, the inventors have found that immunocompetent cells superior in immunity-inducing effect, proliferative potential, survival capacity and the ability to accumulate a T cell to the conventional immunocompetent cells can be generated, and thereby completed the present invention.

Specifically, the present invention is as disclosed in the following items (1) to (9):

(1) An immunocompetent cell expressing a cell surface molecule specifically recognizing a cancer antigen, interleukin 7 (IL-7), and CCL19.
(2) The immunocompetent cell according to (1), wherein the cell surface molecule specifically recognizing a cancer antigen is T cell receptor specifically recognizing the cancer antigen.
(3) The immunocompetent cell according to (1) or (2), wherein the immunocompetent cell is a T cell.
(4) The immunocompetent cell according to any one of (1) to (3), wherein the cancer antigen is WT1, MART-1, NY-ESO-1, MAGE-A1, MAGE-A3, MAGE-A4, Glypican-3, KIF20A, Survivin, AFP-1, gp100, MUC1, PAP-10, PAP-5, TRP2-1, SART-1, VEGFR1, VEGFR2, NEIL3, MPHOSPH1, DEPDC1, FOXM1, CDH3, TTK, TOMM34, URLC10, KOC1, UBE2T, TOPK, ECT2, MESOTHELIN, NKG2D, P1A, GD2, or GM2.
(5) An expression vector for generating an immunocompetent cell according to any one of (1) to (4), the expression vector being any of the following expression vectors (a) to (e):
(a) an expression vector containing a nucleic acid encoding a cell surface molecule specifically recognizing a cancer antigen, a nucleic acid encoding IL-7, and a nucleic acid encoding CCL19;
(b) the following two expression vectors (b-1) and (b-2):
  (b-1) an expression vector containing a nucleic acid encoding a cell surface molecule specifically recognizing a cancer antigen; and
  (b-2) an expression vector containing a nucleic acid encoding IL-7 and a nucleic acid encoding CCL19;
(c) the following two expression vectors (c-1) and (c-2):
  (c-1) an expression vector containing a nucleic acid encoding a cell surface molecule specifically recognizing a cancer antigen, and a nucleic acid encoding IL-7; and
  (c-2) an expression vector containing a nucleic acid encoding CCL19;
(d) the following two expression vectors (d-1) and (d-2):
  (d-1) an expression vector containing a nucleic acid encoding IL-7; and
  (d-2) an expression vector containing a nucleic acid encoding a cell surface molecule specifically recognizing a cancer antigen, and a nucleic acid encoding CCL19; and
(e) the following three expression vectors (e-1), (e-2) and (e-3):
  (e-1) an expression vector containing a nucleic acid encoding a cell surface molecule specifically recognizing a cancer antigen;
  (e-2) an expression vector containing a nucleic acid encoding IL-7; and
  (e-3) an expression vector containing a nucleic acid encoding CCL19.
(6) The expression vector according to (5), wherein the cell surface molecule specifically recognizing a cancer antigen is T cell receptor specifically recognizing the cancer antigen.
(7) The expression vector according to (5) or (6), wherein the nucleic acid encoding a cell surface molecule specifically recognizing a cancer antigen, the nucleic acid encoding IL-7, and the nucleic acid encoding CCL19 in the expression vector (a)
the nucleic acid encoding IL-7 and the nucleic acid encoding CCL19 in the expression vector (b-2) the nucleic acid encoding a cell surface molecule specifically recognizing a cancer antigen, and the nucleic acid encoding IL-7 in the expression vector (c-1), or
the nucleic acid encoding a cell surface molecule specifically recognizing a cancer antigen, and the nucleic acid encoding CCL19 in the expression vector (d-2)
are linked via a sequence encoding a self-cleaving peptide.
(8) The expression vector according to any one of (5) to (7), wherein the expression vector contains a nucleic acid encoding a suicide gene.
(9) An anticancer agent comprising an immunocompetent cell according to any one of (1) to (4) and a pharmaceutically acceptable additive.

Effect of the Invention

The immunocompetent cell expressing a cell surface molecule specifically recognizing a cancer antigen, IL-7, and CCL19 (hereinafter, also referred to as the "IL-7× CCL19-expressing immunocompetent cell") according to the present invention has antitumor activity, and use of this immunocompetent cell enables the suppression of decrease in survival rate caused by tumor formed by a cancer cell having the antigen specifically recognized by the cell surface molecule. Also, use of the expression vector of the present invention enables the generation of an immunocompetent cell that possesses all of proliferative potential, survival capacity and the ability to accumulate a T cell.

BRIEF DESCRIPTION OF DRAWINGS

FIG. 1 is a diagram showing the map of an IL-7×CCL19 expression vector.
FIG. 2A is a diagram showing results of examining the cell number of an IL-7/CCL19-expressing T cell.
FIG. 2B is a diagram showing results of examining the survival rate of the IL-7/CCL19-expressing T cell.
FIG. 3 is a diagram showing results of a T cell migration test using the IL-7/CCL19-expressing T cell.
FIG. 4 is a diagram showing the map of an IL-7×CCL19× HSV-TK expression vector.
FIG. 5 is a diagram showing the map of a TCR×IL-7× CCL19 expression vector.
FIG. 6 is a diagram showing the map of an IL-7×CCL19× eGFP expression vector.
FIG. 7 is a diagram showing the survival rates of an untreated mouse, a mouse given a P1A-specific TCR/eGFP-expressing T cell, and a mouse given a P1A-specific TCR/ IL-7/CCL19/eGFP-expressing T cell.
FIG. 8 is a diagram showing results of examining the tumor volumes of an untreated mouse, a mouse given a P1A-specific TCR/eGFP-expressing T cell, and a mouse given a P1A-specific TCR/IL-7/CCL19/eGFP-expressing T cell.

MODE OF CARRYING OUT THE INVENTION

The IL-7×CCL19-expressing immunocompetent cell of the present invention is not particularly limited as long as the immunocompetent cell expresses a cell surface molecule specifically recognizing a cancer antigen, interleukin 7 (IL-7), and CCL19. The IL-7×CCL19-expressing immunocompetent cell of the present invention may further express other regulatory factors of immune function, such as IL-15, CCL21, IL-2, IL-4, IL-12, IL-13, IL-17, IL-18, IP-10, CCL4, Flt3L, interferon-gamma, MIP-1 alpha, GM-CSF, M-CSF, TGF-beta, and TNF-alpha.

The cancer antigen means a substance, such as a protein or a glycolipid, which is more highly expressed in a cancer cell than in a normal cell or specifically expressed in a cancer cell. Examples of such a cancer antigen can include a tumor-associated antigen, a cancer testis antigen, an angiogenesis-associated antigen, and an epitope peptide of a cancer neoantigen ascribable to gene mutation and can specifically include, but are not limited to, a protein such as WT1, MART-1, NY-ESO-1, MAGE-A1, MAGE-A3, MAGE-A4, Glypican-3, KIF20A, Survivin, AFP-1, gp100, MUC1, PAP-10, PAP-5, TRP2-1, SART-1, VEGFR1, VEGFR2, NEIL3, MPHOSPH1, DEPDC1, FOXM1, CDH3, TTK, TOMM34, URLC10, KOC1, UBE2T, TOPK, ECT2, MESOTHELIN, NKG2D, and P1A, and a glycolipid such as GD2 and GM2.

Examples of the cell surface molecule specifically recognizing a cancer antigen can include a cell surface receptor, an artificial receptor, and an adhesion factor specifically recognizing the cancer antigen and can preferably include a molecule that confers the ability to specifically mark cancer through its expression on cell surface, such as T cell receptor specifically recognizing the cancer antigen and chimeric antigen receptor (CAR) specifically recognizing the cancer antigen, more preferably TCR. TCR may be a heterodimer consisting of an alpha chain and a beta chain (alpha-beta TCR) or may be a heterodimer consisting of a gamma chain and a delta chain (gamma-delta TCR) as long as TCR specifically recognizes the cancer antigen. The cell surface molecule specifically recognizing a cancer antigen may indirectly recognize the cancer antigen as long as the recognition is specific. For example, a molecule (e.g., an antibody) specifically recognizing the cancer antigen is administered to a subject concurrently or continuously with the immunocompetent cell of the present invention, and the immunocompetent cell of the present invention is capable of indirectly specifically recognizing the cancer antigen, by recognizing the molecule (e.g., an antibody) or recognizing a tag labeling the molecule (e.g., an antibody). In the case of recognizing the antibody, examples of the cell surface molecule include CD16. Examples of the tag labeling the molecule (e.g., an antibody) include FITC.

The type of the immunocompetent cell for the IL-7× CCL19-expressing immunocompetent cell of the present invention can be any cell involved in immune response. Examples thereof can include: a lymphoid cell such as a T cell, a natural killer cell (NK cell), and a B cell; an antigen-presenting cell such as a monocyte, a macrophage, and a dendritic cell; and a granulocyte such as a neutrophil, an eosinophil, a basophil, and a mast cell and can preferably include a mammal (e.g., human, dog, cat, pig, or mouse)-derived T cell, more preferably a human-derived T cell. Alternatively, the T cell can be obtained by isolation and purification from a body fluid such as blood or bone marrow fluid, a tissue of the spleen, the thymus, lymph nodes, or the like, or an immunocyte infiltrating a cancer tissue of primary tumor, metastatic tumor, cancerous ascites, or the like. A T cell generated from an ES cell or an iPS cell may be used. Examples of such a T cell can include an alpha-beta T cell, a gamma-delta T cell, a $CD8^+$ T cell, a $CD4^+$ T cell, a tumor-infiltrating T cell, a memory T cell, a naive T cell, and a NKT cell.

Examples of the method for generating the IL-7×CCL19-expressing immunocompetent cell of the present invention can include a generation method which involves introducing the expression vector of the present invention mentioned later to an immunocompetent cell. Alternative examples thereof can include a generation method which involves introducing a vector for the expression of a cell surface molecule specifically recognizing a cancer antigen, interleukin 7 (IL-7), and/or CCL19 to a fertilized egg, an ES cell, or an iPS cell, and then inducing the expression, and a generation method which involves further introducing, if necessary, a vector for the expression of a cell surface molecule specifically recognizing a cancer antigen, interleukin 7 (IL-7), and/or CCL19, to an immunocompetent cell obtained by separation from a transgenic mammal expressing the cell surface molecule specifically recognizing a cancer antigen by gene transfection.

Examples of the generation method which involves introducing the expression vector of the present invention mentioned later to the immunocompetent cell can include, but are not particularly limited to, an introduction method by a method known in the art, such as a viral infection method, a calcium phosphate method, lipofection, microinjection, and electroporation and can preferably include an introduction method by a viral infection method.

Examples of the viral infection method can include a method which involves transfecting a packaging cell such as a GP2-293 cell (manufactured by Takara Bio Inc.), a Plat-GP cell (manufactured by Cosmo Bio Co., Ltd.), a PG13 cell (ATCC CRL-10686), or a PA317 cell (ATCC CRL-9078) with the expression vector of the present invention and a packaging plasmid to generate a recombinant virus and infecting an immunocompetent cell with the recombinant virus. The viral infection method may be performed using a commercially available kit such as Retrovirus packaging Kit Eco (manufactured by Takara Bio Inc.).

The immunocompetent cell of the present invention may be generated by integrating a polynucleotide comprising nucleotide sequences encoding a cell surface molecule specifically recognizing a cancer antigen, IL-7, and CCL19 into the genome of a cell by use of a gene editing technique known in the art such the promoter can be expressed under the control of an appropriate promoter. Examples of the gene editing technique known in the art include a technique using endonuclease such as zinc finger nuclease, TALEN (transcription activator-like effector nuclease), CRISPR (clustered regularly interspaced short palindromic repeat)-Cas system. In the case of allowing the immunocompetent cell of the present invention to express an additional foreign protein, a polynucleotide comprising a nucleotide sequence encoding the additional foreign protein may be similarly integrated into the genome of the cell by use of the gene editing technique such that the promoter can be expressed under the control of an appropriate promoter. Examples of the method for integrating the polynucleotide into the genome of the cell such that the promoter can be expressed under the control of an appropriate promoter include: a method which involves integrating a polynucleotide in which nucleotide sequences encoding a cell surface molecule specifically recognizing a cancer antigen, IL-7, and CCL19 (or an additional protein) are functionally linked downstream of an appropriate promoter (i.e., a polynucleotide in which coding sequences are linked such that the factors (or the additional protein) can be expressed under the control of the promoter) into a noncoding region or the like of the cell genome; and a method which involves integrating a polynucleotide comprising nucleotide sequences encoding a cell surface molecule specifically recognizing a cancer antigen, IL-7, and CCL19 (or an additional protein) downstream of an endogenous promoter of the cell genome. Examples of the endogenous promoter include TCRα and TCRβ promoters.

The IL-7×CCL19-expressing immunocompetent cell of the present invention may also be allowed to express herpes simplex virus thymidine kinase (HSV-TK) or inducible caspase 9 mentioned later.

The IL-7×CCL19-expressing immunocompetent cell of the present invention expresses a cell surface molecule specifically recognizing a cancer antigen, IL-7, and CCL19. Therefore, The IL-7×CCL19-expressing immunocompetent cell of the present invention has high proliferative potential, survival capacity, and the ability to accumulate an intrinsic T cell and is applicable to adoptive immunotherapy using various immunocompetent cells. Examples of the adoptive immunotherapy include, but are not limited to, dendritic cell therapy, NK cell therapy, gamma-delta T cell therapy, alpha-beta T cell therapy, CTL therapy, and TIL therapy. An exemplary method can involve introducing the expression vector of the present invention mentioned later to an immunocompetent cell collected from a patient, amplifying the immunocompetent cell, and administering the immunocompetent cell to the patient. Hereinafter, specific examples will be given, though the present invention is not limited thereby. The dendritic cell therapy comprises the step of taking up a surgically extracted cancer tissue or a lysate thereof into a dendritic cell differentiated from a monocyte collected from a patient, and administering the dendritic cell into the body of the patient and may comprise the step of introducing the expression vector of the present invention into the dendritic cell. In this context, an epitope peptide of a cancer antigen molecule can also be artificially synthesized and used instead of the cancer tissue or the lysate. The NK cell therapy comprises the step of treating a lymphocyte collected from a patient with a plurality of stimulatory substances such as IL-2 to activate and amplify a NK cell, which is then administered to the patient and may comprise the step of introducing the vector of the present invention to the NK cell. Combined use of an antibody drug against cancer with the activated NK cell can be expected to produce an effect of efficiently attacking a cancer cell. The gamma-delta T cell therapy comprises the step of culturing and stimulating a lymphocyte collected from a patient using IL-2 or zoledronic acid to amplify a gamma-delta T cell, which is then administered to the patient and may comprise the step of introducing the expression vector of the present invention to the gamma-delta T cell. The alpha-beta T cell therapy comprises the step of culturing a lymphocyte harvested from a patient with an anti-CD3 antibody or IL-2 and administering an activated alpha-beta T cell to the patient and may comprise the step of introducing the expression vector of the present invention to the alpha-beta T cell. The CTL therapy comprises the step of stimulating a lymphocyte harvested from a patient with a cancer cell collected from the patient, culturing the lymphocyte by the addition of an anti-CD3 antibody or IL-2 to amplify CTL specific for the cancer cell, which is then administered to the patient and may comprise the step of introducing the expression vector of the present invention to the CTL. An antigen-presenting cell that presents a cancer antigen epitope peptide can also be used instead of the cancer cell. The TIL therapy comprises the step of harvesting a lymphocyte from a cancer tissue collected from a patient, stimulating and culturing the lymphocyte with IL-2 or the like, and administering the lymphocyte to the patient and may comprise the step of introducing the expression vector of the present invention to the lymphocyte.

The expression vector of the present invention is any of the following expression vectors (a) to (e) for generating the IL-7×CCL19-expressing immunocompetent cell of the present invention:

(a) an expression vector containing a nucleic acid encoding a cell surface molecule specifically recognizing a cancer antigen, a nucleic acid encoding IL-7, and a nucleic acid encoding CCL19;

(b) the following two expression vectors (b-1) and (b-2):
   (b-1) an expression vector containing a nucleic acid encoding a cell surface molecule specifically recognizing a cancer antigen; and
   (b-2) an expression vector containing a nucleic acid encoding IL-7 and a nucleic acid encoding CCL19;

(c) the following two expression vectors (c-1) and (c-2):
   (c-1) an expression vector containing a nucleic acid encoding a cell surface molecule specifically recognizing a cancer antigen, and a nucleic acid encoding IL-7; and
   (c-2) an expression vector containing a nucleic acid encoding CCL19;

(d) the following two expression vectors (d-1) and (d-2):
   (d-1) an expression vector containing a nucleic acid encoding IL-7; and
   (d-2) an expression vector containing a nucleic acid encoding a cell surface molecule specifically recognizing a cancer antigen, and a nucleic acid encoding CCL19; and (e) the following three expression vectors (e-1), (e-2) and (e-3):
   (e-1) an expression vector containing a nucleic acid encoding a cell surface molecule specifically recognizing a cancer antigen;
   (e-2) an expression vector containing a nucleic acid encoding IL-7; and
   (e-3) an expression vector containing a nucleic acid encoding CCL19.

The expression vector of the present invention may further contain nucleic acids encoding other regulatory factors of immune function such as IL-15, CCL21, IL-2, IL-4, IL-12, IL-13, IL-17, IL-18, IP-10, CCL4, Flt3L, interferon-gamma, MIP-1 alpha, GM-CSF, M-CSF, TGF-beta, TNF-alpha.

Examples of the nucleic acid encoding a cell surface molecule specifically recognizing a cancer antigen, the nucleic acid encoding interleukin 7 (IL-7), and the nucleic acid encoding CCL19 can include respective mammal-derived nucleic acids and can preferably include human-derived nucleic acids. The respective nucleic acids can be appropriately selected according to the type of the cell to which the expression vector of the present invention is introduced. Sequence information on these respective nucleic acids can be appropriately obtained by the search of a document known in the art or a database such as NCBI (ncbi.nlm.nih.gov/guide/).

Examples of the nucleic acid encoding a cell surface molecule specifically recognizing a cancer antigen can preferably include a human-derived nucleic acid. Examples of such a nucleic acid encoding a cell surface molecule specifically recognizing a cancer antigen can include a nucleic acid encoding T cell receptor (TCR) or a nucleic acid encoding chimeric antigen receptor (CAR). This nucleic acid may be a naturally derived nucleic acid or may be an artificially synthesized nucleic acid and can be appropriately selected according to the type of the cell to which the expression vector of the present invention is introduced. Sequence information thereon can be appropriately obtained by the search of a document known in the art or a database such as NCBI (ncbi.nlm.nih.gov/guide/).

The nucleic acid encoding a cell surface molecule specifically recognizing a cancer antigen, the nucleic acid encoding IL-7 and the nucleic acid encoding CCL19 can be generated by a technique known in the art, such as a chemical synthesis method or a PCR amplification method, based on information on the nucleotide sequence of each encoding nucleic acid. Selected codons for encoding amino acids may be modified in order to optimize nucleic acid expression in a target host cell.

TCR for the nucleic acid encoding TCR may be a heterodimer consisting of an alpha chain and a beta chain (alpha-beta TCR) or may be a heterodimer consisting of a gamma chain and a delta chain (gamma-delta TCR). The nucleic acid encoding alpha-beta TCR comprises both of a nucleic acid encoding the alpha chain of TCR and a nucleic acid encoding the beta chain thereof. The nucleic acid encoding gamma-delta TCR includes both of a nucleic acid encoding the gamma chain of TCR and a nucleic acid encoding the delta chain thereof.

Sequence information on the nucleic acid encoding TCR can be identified from the nucleic acids of the alpha chain and the beta chain as a TCR subunit of CTL induced using a particular antigenic peptide by use of a method known in the art (International Publication No. WO 2007/032255; and Morgan et al., J Immunol, 171, 3288 (2003)). For example, PCR is preferred for analyzing TCR. PCR primers for TCR analysis can be, for example, 5'-R primer (5'-gtctaccaggcat-tcgcttcat-3': SEQ ID NO: 3) as a 5' primer and 3-TRa-C primer (5'-tcagctggaccacagccgcagcgt-3': SEQ ID NO: 4) specific for a TCR alpha chain C region, 3-TRb-C1 primer (5'-tcagaaatcctttctcttgac-3': SEQ ID NO: 5) specific for a TCR beta chain C1 region, or 3-TRbeta-C2 primer (5'-ctagcctctggaatcctttctctt-3': SEQ ID NO: 6) specific for a TCR beta chain C2 region as a 3' primer, though the primers are not limited thereto. A TCR derivative can bind, with high binding activity, to a target cell presenting an antigenic peptide and can arbitrarily mediate in vivo and in vitro the efficient killing of the target cell presenting an antigenic peptide.

The nucleic acid encoding TCR is, for example, a nucleic acid encoding TCR such as MART1-specific TCR (Cancer Res. 54, 5265-5268 (1994)), MAGE-A3-specific TCR (Anticancer Res., 20, 1793-1799 (2000)), gp100-specific TCR (J. Immunol. 170, 2186-2194 (2003)), NY-ESO-1-specific TCR (J. Immunol., 174, 4415-4423 (2005)), WT1-specific TCR (Blood, 106, 470-476 (2005)), MAGE-A1-specific TCR (Int. Immunol., 8, 1463-1466 (1996)), or P1A-specific TCR (Sarma, S., Y. Guo, Y. Guilloux, C. Lee, X.-F. Bai, Y. Liu. 1999. Cytotoxic T lymphocytes to an unmutated tumor antigen P1A: normal development but restrained effector function. J. Exp. Med. 189: 811) and may be a nucleotide sequence having 80% or higher, preferably 85% or higher, more preferably 90% or higher, further preferably 95% or higher, most preferably 98% or higher identity to a nucleotide sequence encoding any of the TCRs described in the documents as long as the TCR can recognize the antigen molecule bound with a MHC molecule and can activate a T cell. In the nucleotide sequence encoding any of the TCRs described in the documents, a sequence encoding CDR is identified, and a nucleotide sequence that maintains the sequence encoding CDR and has a sequence, other than the sequence encoding CDR, having 60% or higher, preferably 70% or higher, more preferably 80% or higher, further preferably 90% or higher, most preferably 95% or higher identity to the nucleotide sequence encoding any of the TCRs described in the documents may be used.

Examples of the nucleic acid encoding IL-7 can include a nucleotide sequence encoding the amino acid sequence represented by SEQ ID NO: 1. The nucleic acid encoding IL-7 may be a nucleotide sequence having 80% or higher, preferably 85% or higher, more preferably 90% or higher, further preferably 95% or higher, most preferably 98% or higher identity to the nucleotide sequence encoding the amino acid sequence represented by SEQ ID NO: 1 as long as the IL-7 has a cell proliferation rate- or cell survival rate-enhancing effect. Examples of the nucleic acid encoding CCL19 can include a nucleotide sequence encoding the amino acid sequence represented by SEQ ID NO: 2. A nucleotide sequence having 80% or higher, preferably 85% or higher, more preferably 90% or higher, further preferably 95% or higher, most preferably 98% or higher identity to the nucleotide sequence encoding the amino acid sequence represented by SEQ ID NO: 2 may be used as long as the CCL19 has a chemoattractive effect on a cell.

The expression vector of the present invention may also contain a nucleic acid encoding a suicide gene. The suicide gene means a gene having a function of directly or secondarily inducing a substance having cytotoxicity and killing a cell expressing this suicide gene. The expression vector of the present invention containing the nucleic acid encoding a suicide gene can regulate an immunocompetent cell in vivo by the administration of a drug activating the function of the suicide gene according to the course of treatment of cancer, for example, when tumor has disappeared. IL-7 or CCL19, unlike other cytokines, is less likely to cause cytokine release syndrome or tumorigenic transformation of a transgenic cell as an adverse reaction. However, as a result of enhancing the function of an immunocompetent cell introduced with the expression vector of the present invention, a cytokine or the like released upon attack on a target cancer tissue may unexpectedly influence its surrounding tissues. In such a case, the expression vector of the present invention containing the nucleic acid encoding a suicide gene is capable of reliably reducing the risk of causing cytokine release syndrome.

Examples of the suicide gene can include genes encoding herpes simplex virus thymidine kinase (HSV-TK) and inducible caspase 9 described in documents given below. Examples of the drugs activating the function of these genes can include ganciclovir for the former and a CID (chemical induction of dimerization) compound AP1903 for the latter (Cooper L J., et al., Cytotherapy. 2006; 8 (2): 105-17; Jensen M. C. et al., Biol Blood Marrow Transplant. 2010 September; 16 (9): 1245-56; Jones B S. Front Pharmacol. 2014 Nov. 27; 5: 254; Minagawa K., Pharmaceuticals (Basel). 2015 May 8; 8 (2): 230-49; and Bole-Richard E., Front Pharmacol. 2015 Aug. 25; 6: 174).

In the expression vector (a) containing a nucleic acid encoding a cell surface molecule specifically recognizing a cancer antigen, a nucleic acid encoding IL-7, and a nucleic acid encoding CCL19 as the vector of the present invention, any of the nucleic acids may be arranged upstream or downstream of any of the nucleic acids. Specifically, the case of containing a nucleic acid encoding TCR as the nucleic acid encoding a cell surface molecule specifically recognizing a cancer antigen will be taken as an example.

The expression vector may have the nucleic acid encoding TCR, the nucleic acid encoding IL-7 and the nucleic acid encoding CCL19, may have the nucleic acid encoding TCR, the nucleic acid encoding CCL19 and the nucleic acid encoding IL-7, may have the nucleic acid encoding IL-7, the nucleic acid encoding CCL19 and the nucleic acid encoding TCR, may have the nucleic acid encoding IL-7, the nucleic acid encoding TCR and the nucleic acid encoding CCL19, may have the nucleic acid encoding CCL19, the nucleic acid encoding TCR and the nucleic acid encoding IL-7, or may have the nucleic acid encoding CCL19, the nucleic acid encoding IL- and the nucleic acid encoding TCR, in order from upstream.

In the expression vector (b-2) containing a nucleic acid encoding IL-7 and a nucleic acid encoding CCL19 as the vector of the present invention, the arrangement of the nucleic acid encoding IL-7 and the nucleic acid encoding CCL19 is not particularly limited, and the nucleic acid encoding CCL19 may be arranged upstream or downstream of the nucleic acid encoding IL-7.

In the expression vector (c-1) containing a nucleic acid encoding a cell surface molecule specifically recognizing a cancer antigen, and a nucleic acid encoding IL-7 as the vector of the present invention, the arrangement of the nucleic acid encoding a cell surface molecule specifically recognizing a cancer antigen and the nucleic acid encoding IL-7 is not particularly limited, and the nucleic acid encoding IL-7 may be arranged upstream or downstream of the nucleic acid encoding a cell surface molecule specifically recognizing a cancer antigen.

In the expression vector (d-2) containing a nucleic acid encoding a cell surface molecule specifically recognizing a cancer antigen, and a nucleic acid encoding CCL19 as the vector of the present invention, the arrangement of the nucleic acid encoding a cell surface molecule specifically recognizing a cancer antigen and the nucleic acid encoding CCL19 is not particularly limited, and the nucleic acid encoding CCL19 may be arranged upstream or downstream of the nucleic acid encoding a cell surface molecule specifically recognizing a cancer antigen.

The nucleic acid encoding a cell surface molecule specifically recognizing a cancer antigen, the nucleic acid encoding IL-7 and the nucleic acid encoding CCL19 may respectively be transcribed by different promoters or may be transcribed by one promoter using an internal ribozyme entry site (IRES) or self-cleaving 2A peptide.

The expression vector of the present invention may comprise an arbitrary nucleic acid between the nucleic acid encoding IL-7 and the nucleic acid encoding CCL19 in the case of transcribing these nucleic acids by one promoter using an internal ribozyme entry site (IRES) or self-cleaving 2A peptide, between the nucleic acid encoding a cell surface molecule specifically recognizing a cancer antigen and the nucleic acid encoding IL-7 and the nucleic acid encoding CCL19 in the case of comprising the nucleic acid encoding a cell surface molecule specifically recognizing a cancer antigen, between a nucleic acid encoding an alpha chain and a nucleic acid encoding a beta chain in the case of comprising a nucleic acid encoding alpha-beta TCR, or between a nucleic acid encoding a gamma chain and a nucleic acid encoding a delta chain in the case of comprising a nucleic acid encoding gamma-delta TCR, as long as each nucleic acid can be expressed. These nucleic acids are preferably linked via a sequence encoding a self-cleaving peptide (2A peptide) or IRES, preferably a sequence encoding 2A peptide. The linkage using this sequence enables the efficient expression of each nucleic acid.

In the case of containing a nucleic acid encoding a suicide gene, the position of the suicide gene is not particularly limited, and the suicide gene may be located, for example, via a sequence encoding 2A peptide or IRES, downstream of a promoter for the expression of the nucleic acid encoding a cell surface molecule specifically recognizing a cancer antigen, the nucleic acid encoding IL-7, or the nucleic acid encoding CCL19 and upstream or downstream of each of these nucleic acids, or may be located downstream of a different promoter.

The 2A peptide is a virus-derived self-cleaving peptide and is characterized in that G-P (position of 1 residue from the C terminus) in the amino acid sequence represented by SEQ ID NO: 7 is cleaved in the endoplasmic reticulum (Szymczak et al., Expert Opin. Biol. Ther. 5 (5): 627-638 (2005)). Therefore, nucleic acids incorporated to flank the 2A peptide are intracellularly expressed independently from each other.

The 2A peptide is preferably 2A peptide derived from picornavirus, rotavirus, insect virus, Aphthovirus, or *Trypanosoma* virus, more preferably picornavirus-derived 2A peptide (F2A) shown in SEQ ID NO: 8.

The vector for the expression vector of the present invention may be linear or circular and may be a non-viral vector such as a plasmid, a viral vector, or a vector based on a transposon. Such a vector may contain control sequences such as a promoter and a terminator, and a selective marker sequence such as a drug resistance gene or a reporter gene. The nucleic acid encoding IL-7 and the nucleic acid encoding CCL19 are operably located downstream of the promoter sequence so that each nucleic acid can be efficiently transcribed.

Examples of the promoter can include: a virus-derived promoter such as retrovirus LTR promoter, SV40 early promoter, cytomegalovirus promoter, herpes simplex virus thymidine kinase promoter; and a mammal-derived promoter such as phosphoglycerate kinase (PGK) promoter, Xist promoter, β-actin promoter, and RNA polymerase II promoter. Alternatively, tetracycline-responsive promoter which is induced by tetracycline, Mx1 promoter which is induced by interferon, or the like may be used. Use of the promoter which is induced by a particular substance in the expression vector of the present invention enables the regulation of induction of IL-7 and CCL19 expression in response to the course of treatment of cancer.

Examples of the viral vector can include a retrovirus vector, a lentivirus vector, an adenovirus vector, and an adeno-associated virus vector and can preferably include a retrovirus vector, more preferably a pMSGV vector (Tamada k et al., Clin Cancer Res 18: 6436-6445 (2002)) and a pMSCV vector (manufactured by Takara Bio Inc.). By use of a retrovirus vector, a transgene is integrated into the genome of a host cell and can therefore be expressed stably for a long period.

In order to confirm the containment of the expression vector of the present invention in the immunocompetent cell, for example, the expression of TCR can be examined by flow cytometry, Northern blotting, Southern blotting, PCR such as RT-PCR, ELISA, or Western blotting when the expression vector contains a nucleic acid encoding TCR, and the expression of a marker gene inserted in the expression vector of the present invention can be examined when the expression vector contains the marker gene.

When the expression vector contained in the IL-7× CCL19-expressing immunocompetent cell of the present invention contains a nucleic acid encoding TCR, the variable region of TCR to be expressed is extracellularly positioned.

The TCR-expressing immunocompetent cell having this variable region of TCR is capable of recognizing the antigen molecule bound with a MHC molecule.

The anticancer agent of the present invention is not particularly limited as long as the anticancer agent comprises the IL-7×CCL19-expressing immunocompetent cell of the present invention and a pharmaceutically acceptable additive. Examples of the additive can include saline, buffered saline, a cell culture medium, dextrose, injectable water, glycerol, ethanol, and a combination thereof, a stabilizer, a solubilizer and a surfactant, a buffer and an antiseptic, a tonicity agent, a filler, and a lubricant.

The anticancer agent of the present invention can be administered to a test subject in need of treatment of cancer by use of a method known to those skilled in the art. Examples of the administration method can include intravenous, intratumoral, intracutaneous, subcutaneous, intramuscular, intraperitoneal, intraarterial, intramedullary, intracardiac, intraarticular, intrasynovial, intracranial, intrathecal, and subarachnoidal (spinal fluid) injection.

The amount of the IL-7×CCL19-expressing immunocompetent cell of the present invention contained in the anticancer agent to be administered can be appropriately adjusted according to the type, position, and severity of cancer, the age, body weight, and condition of the test subject to receive treatment, etc. Examples thereof can preferably include $1\times10^4$ to $1\times10^{10}$ cells, preferably $1\times10^5$ to $1\times10^9$ cells, more preferably $5\times10^6$ to $5\times10^8$ cells, in a single dose.

In an exemplary method, the anticancer agent to be administered can be independently administered 4 times, 3 times, twice, or once a day, at a 1-day, 2-day, 3-day, 4-day, or 5-day interval, once a week, at a 7-day, 8-day, or 9-day interval, twice a week, once a month, or twice a month.

The cancer for the anticancer agent of the present invention or a method for treating cancer mentioned later may be solid cancer or blood cancer. Examples thereof can include: cancer such as adenocarcinoma, squamous cell cancer, adenosquamous cancer, undifferentiated cancer, large-cell cancer, small-cell cancer, skin cancer, breast cancer, prostate cancer, urinary bladder cancer, vaginal cancer, neck cancer, uterine cancer, liver cancer, kidney cancer, pancreatic cancer, spleen cancer, lung cancer, tracheal cancer, bronchial cancer, colon cancer, small intestine cancer, stomach cancer, esophageal cancer, gallbladder cancer, testis cancer, and ovary cancer; cancer of a bone tissue, a cartilage tissue, a fat tissue, a muscle tissue, a vascular tissue, and a hematopoietic tissue; sarcoma such as chondrosarcoma, Ewing's sarcoma, malignant hemangioendothelioma, malignant schwannoma, osteosarcoma, and soft tissue sarcoma; blastoma such as hepatoblastoma, medulloblastoma, nephroblastoma, neuroblastoma, pancreatoblastoma, pleuropulmonary blastoma, and retinoblastoma; embryonic cell tumor; lymphoma; and leukemia.

The anticancer agent of the present invention can be used in combination with an additional anticancer agent. Examples of the additional anticancer agent can include: an alkylating agent such as cyclophosphamide, bendamustine, ifosfamide, and dacarbazine; an antimetabolite such as pentostatin, fludarabine, cladribine, methotrexate, 5-fluorouracil, 6-mercaptopurine, and enocitabine; a molecular targeting drug such as rituximab, cetuximab, and trastuzumab; a kinase inhibitor such as imatinib, gefitinib, erlotinib, afatinib, dasatinib, sunitinib, and trametinib; a proteasome inhibitor such as bortezomib; a calcineurin inhibitor such as cyclosporine and tacrolimus; an anticancer antibiotic such as idarubicin, doxorubicin, and mitomycin C; a vegetable alkaloid such as irinotecan and etoposide; a platinum-containing drug such as cisplatin, oxaliplatin, and carboplatin; a hormone therapeutic such as tamoxifen and bicalutamide; and an immunoregulatory drug such as interferon, nivolumab, and pembrolizumab and can preferably include an alkylating agent and an antimetabolite.

Examples of the method for "using the anticancer agent of the present invention in combination with the additional anticancer agent" can include a method using the additional anticancer agent in the treatment, followed by use of the anticancer agent of the present invention, a method concurrently using the anticancer agent of the present invention and the additional anticancer agent, and a method using the anticancer agent of the present invention in the treatment, followed by use of the additional anticancer agent and can preferably include a method using the additional anticancer agent in the treatment, followed by use of the anticancer agent of the present invention. The combined use of the anticancer agent of the present invention and the additional anticancer agent further improves a therapeutic effect on cancer and can also reduce the adverse reaction of each anticancer agent by decreasing the administration frequency or dose of the anticancer agent. Also, the additional anticancer agent may be contained in the anticancer agent of the present invention.

Examples of alternative aspect 1 of the present invention can include 1) a method for treating cancer, comprising administering an immunocompetent cell expressing a cell surface molecule specifically recognizing a cancer antigen, interleukin 7 (IL-7), and CCL19 to a patient in need of treatment of cancer, 2) an immunocompetent cell expressing a cell surface molecule specifically recognizing a cancer antigen, interleukin 7 (IL-7), and CCL19, for use as an anticancer agent, and 3) use of an immunocompetent cell expressing a cell surface molecule specifically recognizing a cancer antigen, interleukin 7 (IL-7), and CCL19, for the preparation of an anticancer agent.

Examples of alternative aspect 2 of the present invention can include a kit for the generation of an immunocompetent cell expressing a cell surface molecule specifically recognizing a cancer antigen, interleukin 7 (IL-7), and CCL19, comprising the expression vector of the present invention. The kit is not particularly limited as long as the kit comprises the expression vector of the present invention. The kit may comprise an instruction manual for the generation of the IL-7×CCL19-expressing immunocompetent cell of the present invention, and a reagent for use in the introduction of the expression vector of the present invention to an immunocompetent cell.

Example 1

(Selection of Regulatory Factors of Immune Function)

At least several hundred different types of molecules that can regulate the function of T cells are present in vivo. The inventors first selected IL-7 and CCL19 from among an enormous number of combinations on the basis of the previous findings or experiments, as regulatory molecules for further enhancing the immune function-regulating effect of immunocompetent cells, and also selected the combination of these two molecules, i.e., the combination of IL-7 and CCL19, not each alone. The inventors generated a vector for the expression of these regulatory factors of immunocompetent cell immune function.

(Generation of Expression Vector for Expression of IL-7 and CCL19—1)

An anti-FITC CAR DNA fragment (SEQ ID NO: 9) encoding anti-FITC CAR consisting of anti-FITC scFv, a mouse CD8 transmembrane region, and mouse CD28-4-1BB-CD3 intracellular signal motifs, a F2A-MCS DNA fragment (SEQ ID NO: 10) encoding 2A peptide (F2A) shown in SEQ ID NO: 8 and a multicloning site (MCS) following the peptide, and an IL-7-F2A-CCL19 DNA fragment (SEQ ID NO: 11) encoding mouse IL-7 (without a stop codon) and F2A and mouse CCL19 following the mouse IL-7 were artificially synthesized (Life Technologies Corp.).

In order to generate a vector for the expression of IL-7 and CCL19, the anti-FITC CAR DNA fragment and the F2A-MCS DNA fragment were linked to generate an anti-FITC CAR-F2A-MCS construct. Then, the generated construct was cloned into a pMSGV retrovirus expression vector (Tamada k et al., Clin Cancer Res 18: 6436-6445 (2002)) to generate a pMSGV vector containing anti-FITC CAR-F2A-MCS. The IL-7-F2A-CCL19 DNA fragment was inserted to the MCS of the pMSGV vector by restriction enzyme (NsiI and SalI) treatment and ligation to obtain a pMSGV vector containing anti-FITC CAR-F2A-IL-7-F2A-CCL19 (IL-7×CCL19 expression vector (1)). The map of the obtained vector is shown in FIG. 1. Also, the anti-FITC CAR DNA fragment was cloned into the pMSGV retrovirus expression vector to generate a pMSGV vector free from IL-7 and CCL19 as a control (control vector (1)).

(Generation of Retrovirus Introduced with IL-7×CCL19 Expression Vector)

For the transduction of mouse T cells, retrovirus was generated. A GP2-293 packaging cell line (manufactured by Takara Bio Inc.) was transfected with the aforementioned IL-7×CCL19 expression vector (1) or control vector (1) and a pCL-Eco plasmid (manufactured by Imgenex Corp.) using Lipofectamine 2000 or 3000 (manufactured by Life Technologies Corp.) to generate retrovirus introduced with the IL-7×CCL19 expression vector (1) or the control vector (1).

DMEM supplemented with 10% FCS, 100 U/ml penicillin, and 100 mg/ml streptomycin was used as a culture medium for the GP2-293 cells. RPMI-1640 supplemented with 10% FCS, 100 U/ml penicillin, 100 mg/ml streptomycin, 50 mM 2-mercaptoethanol, and 2 mM L-glutamine was used as a culture medium for T cells used in Examples mentioned later.

(Transduction of Mouse T Cells)

For the transduction of mouse T cells, $3\times10^6$ purified mouse T cells derived from the spleen and lymph nodes were activated for 48 hours with immobilized anti-CD3 mAb (3 μg/ml) and IL-2 (100 IU/ml). Then, the supernatant containing the thus-generated retrovirus introduced with the IL-7×CCL19 expression vector (1) or the control vector (1) was mixed with the activated mouse T cells mentioned above ($1\times10^6$ cells/ml) in a plate coated with 25 μg/ml RetroNectin® (manufactured by Takara Bio Inc.). After centrifugation at 1500 rpm for 2 hours, the cells were cultured for 6 hours in the presence of IL-2 (100 IU/ml). In order to remove the retrovirus from the culture medium, the mouse T cells were recovered, transferred to a fresh growth culture medium (RPMI) containing IL-2 (100 IU/ml), and further cultured for 42 hours to obtain mouse T cells introduced with the IL-7×CCL19 expression vector (1) (IL-7/CCL19-expressing T cells (1)) or mouse T cells introduced with the control vector (1) (control T cells (1)).

(Generation of Expression Vector for Expression of IL-7 and CCL19—2)

A pMSGV vector containing anti-human CD20 CAR-F2A-IL-7-F2A-CCL19 (IL-7×CCL19 expression vector (2)) was generated in the same way as in the preceding section "Generation of expression vector for expression of IL-7 and CCL19—1" except that in the generation of the IL-7×CCL19 expression vector (1) described above, the sequence of the anti-FITC scFv region contained in the sequence represented by SEQ ID NO: 9 was replaced with a sequence of anti-human CD20 scFv (SEQ ID NO: 12) synthesized by Life Technologies Corp. on the basis of the sequence of rituximab. Likewise, a pMSGV vector free from IL-7 and CCL19 (control vector (2)) was generated in the same way as in the preceding section "Generation of expression vector for expression of IL-7 and CCL19—1" except that in the generation of the control vector (1) described above, the sequence of the anti-FITC scFv region contained in the sequence represented by SEQ ID NO: 9 was replaced with the sequence of anti-human CD20 scFv (SEQ ID NO: 12). The IL-7×CCL19 expression vector (2) or the control vector (2) was transferred to mouse T cells using retrovirus in the same way as above to generate IL-7/CCL19-expressing T cells (2) or control T cells (2).

Example 2

(Cell Number and Viability of IL-7/CCL19-Expressing T Cells)

Study was conducted on whether or not IL-7 or CCL19 produced by the IL-7/CCL19-expressing T cells would exert biological function and exhibit an immunity-inducing effect. A sample containing the generated IL-7/CCL19-expressing T cells (2) ($4\times10^3$ cells) or the control T cells (2) was cultured for 5 days. The culture was performed without antigen stimulation with CD20 in order to eliminate the influence of human CD20 CAR on the expression of IL-7 and CCL19. Then, the cell number and the viability were examined using trypan blue. The results are shown in FIGS. 2A and 2B. FIG. 2A shows the cell number, and FIG. 2B shows the viability. The filled column shows the results about the IL-7/CCL19-expressing T cells, and the open column shows the results about the control T cells.

(Results)

As shown in FIGS. 2A and 2B, the cell number and the viability of the IL-7/CCL19-expressing T cells (2) were approximately 5 times and approximately 2 times, respectively, higher than those of the control T cells (2). These results demonstrated that by use of the IL-7/CCL19-expressing T cells prepared by introducing the expression vector of the present invention to T cells, IL-7 or CCL19 exerts biological function and exhibits an immunity-inducing effect.

Example 3

[T Cell Migration Test]

(T Cell Migration Test Using IL-7/CCL19-Expressing T Cells)

The chemoattractive effect of CCL19 was studied by a cell migration test using Transwell. The migration properties of responder T cells were measured by migration through a polycarbonate filter having a pore size of 5 μm using 96-well Transwell® chambers (Costar, manufactured by Corning, Inc.). Specifically, the IL-7/CCL19-expressing T cells (1) or the control T cells (1) were cultured in the lower chamber. The culture was performed without antigen stimulation with FITC in order to eliminate the influence of FITC CAR on the expression of IL-7 and CCL19. The responder T cells were prepared from the spleen or lymph nodes by negative selection using MACS (manufactured by Miltenyi Biotec GmbH). The responder T cells were labeled with CytoTell blue (manufactured by AAT Bioquest, Inc.) and cultured for 3 hours in the upper chamber. The migration from the upper chamber to the lower chamber was examined by flow cytometry (EC800; manufactured by Sony Corp.), and FlowJo software (manufactured by Tree Star, Inc.) was used in data analysis. The results are shown in FIG. 3. In FIG. 3, the filled column shows the results about the IL-7/CCL19-expressing T cells (1), the open column shows the results about the control T cells (1), and the ordinate shows the absolute number of responder T cells that migrated to the lower chamber. Statistically significant difference was studied by the Student's t-test.

(Results)

As shown in FIG. 3, the IL-7/CCL19-expressing T cells (1) allowed T cells to migrate to the lower chamber by approximately 1.8 times as compared with the control T cells (1). In lymphocyte (e.g., T cell) transfer therapy, damage to cancer cells by administered T cells is important as a matter of course, and in addition, it is important to activate endogenous T cells (=host's immunocytes) originally present in a cancer patient and thereby recruit these cells as cells attacking the cancer cells. For this purpose, it is preferred not only to transfer lymphocytes having antitumor activity ab extra but to evoke the active interaction between the transferred T cells and the endogenous T cells by some approach so that the endogenous T cells are accumulated locally to cancer, from the viewpoint of enhancing immunotherapeutic effects. As seen from the results of FIG. 3, the IL-7/CCL19-expressing T cells (1) had the ability to accumulate intrinsic T cells, demonstrating that the active interaction between the transferred T cells and the endogenous T cells can be induced.

The results of FIGS. 2A, 2B, and 3 demonstrated that the T cells expressing IL-7 and CCL19 possess important effects, indispensable for the induction of immunity, of effectively proliferating by IL-7, having a high viability, and accumulating T cells via CCL19, and have an excellent immunity-inducing effect. In short, the expression of the two regulatory molecules, i.e., "IL-7" and "CCL19", in immunocompetent cells was shown to enable improvement in the proliferative potential, the viability, and the immunity-inducing effect of the immunocompetent cells. Furthermore, as mentioned above, the T cells expressing IL-7 and CCL19 possess all of the proliferative potential, the survival capacity, and the ability to accumulate a T cell, suggesting the possibility that these T cells have an effect of infiltrating into cancer tissues on T cells or dendritic cells and a tumor growth inhibitory effect.

Example 4

[Generation of IL-7×CCL19×HSV-TK Expression Vector]

A nucleotide sequence in which nucleotide sequences encoding IL-7 gene, CCL19 gene and a suicide gene HSV-TK are arranged in tandem so as to flank a nucleotide sequence encoding a self-cleaving peptide 2A peptide can be cloned into the multicloning site of a pMSGV1 vector to generate a vector for the expression of IL-7, CCL19, and HSV-TK. The map of this vector is shown in FIG. 4.

Immunocompetent cells introduced with the IL-7× CCL19×HSV-TK expression vector thus generated are capable of regulating immunocompetent cells within a test subject by the administration of ganciclovir to the test subject given the immunocompetent cells.

Example 5

[Generation of TCR×IL-7×CCL19 Expression Vector]

A nucleotide sequence in which nucleotide sequences encoding TCR gene, IL-7 gene and CCL19 gene are arranged in tandem so as to flank a nucleotide sequence encoding a self-cleaving peptide 2A peptide can be cloned into the multicloning site of a pMSGV1 vector to generate a vector for the expression of TCR, IL-7 and CCL19. The map of this vector is shown in FIG. 5.

Immunocompetent cells introduced with the TCR×IL-7× CCL19 expression vector thus generated are capable of specifically binding to not only the cancer antigen present on cancer cell surface but a complex of a cancer antigen-derived peptide presented by MHC within cancer cells and are capable of inducing T cells specific for a wider range of tumor-associated target molecules.

Example 6

[Generation of Expression Vector for Expression of IL-7, CCL19 and eGFP]

An IL-7-F2A-CCL19 DNA fragment encoding mouse IL-7 (without a stop codon) and F2A and mouse CCL19 following the mouse IL-7 was artificially synthesized (Life Technologies Corp.).

In order to generate a vector for the expression of IL-7, CCL19 and eGFP, the IL-7-F2A-CCL19 DNA fragment thus synthesized was inserted to the MCS of a pMSGV retrovirus expression vector having a F2A-eGFP sequence (Tamada k et al., Clin Cancer Res 18: 6436-6445 (2002)) by restriction enzyme (NcoI and EcoRI) treatment and ligation to obtain a pMSGV vector containing an IL-7-F2A-CCL19-F2A-eGFP DNA fragment (SEQ ID NO: 13) (IL-7×CCL19 expression vector (3)). The map of the obtained vector is shown in FIG. 6. Also, a pMSGV vector containing eGFP and containing neither IL-7 nor CCL19 (control vector (3)) was generated as a control. In SEQ ID NO: 13, nucleotide positions 1 to 462 represent a nucleic acid encoding IL-7 (nucleotide positions 1 to 75 represent a signal sequence of IL-7), nucleotide positions 463 to 537 represent a nucleic acid encoding F2A, nucleotide positions 538 to 861 represent a nucleic acid encoding CCL19 (nucleotide positions 538 to 612 represent a signal sequence of CCL19), nucleotide positions 868 to 942 represent a nucleic acid encoding F2A, nucleotide positions 946 to 1662 represent a nucleic acid encoding eGFP, and nucleotide positions 1663 to 1665 represent a stop codon. The amino acid sequence corresponding to the nucleotide sequence represented by SEQ ID NO: 13 is shown in SEQ ID NO: 14. In order to use a restriction enzyme NcoI, thymine (t) at nucleotide position 4 in SEQ ID NO: 13 was replaced with guanine (g) (phenylalanine (F) at amino acid position 2 in SEQ ID NO: 14 was replaced with valine (V)).

[Generation of T Cells Expressing P815 Tumor Antigen P1A-Specific TCR, IL-7, CCL19, and eGFP]

Spleen cells were collected from a transgenic mouse expressing $H-2L^d$-restricted TCR specific for P815 tumor antigen P1A (Sarma, S., Y. Guo, Y. Guilloux, C. Lee, X.-F. Bai, Y. Liu. 1999. J. Exp. Med. 189: 811) obtained from Y. Liu. Mouse T cells expressing P815 tumor antigen P1A-specific TCR derived from the spleen cells (P1A-specific TCR-T cells) were obtained. Then, retrovirus introduced with the IL-7×CCL19 expression vector (3) or the control vector (3) was generated in the same way as in Example 1. The cells activated with P1A peptide for 48 hours were transduced with the spleen cells (3×10⁶ cells/well) including the P1A-specific TCR-T cells to obtain P1A-specific TCR/IL-7/CCL19/eGFP-expressing T cells or P1A-specific TCR/eGFP-expressing T cells. The transduction with each expression vector was confirmed by flow cytometry analysis of detecting eGFP as a surrogate marker. The respective eGFP expression levels of the obtained T cells were 70 to 80% in all experiments.

On day 0, 5×10⁵ cells of P815 mastocytoma suspended in 0.1 ml of HBSS were subcutaneously inoculated to the flank of each 6- to 10-week-old male DBA/2 mouse (n=30). On day 6, the mice were irradiated at a sublethal dose (3 to 5 Gy) for preconditioning. On day 7, the mice were divided into 3 groups (n=10). The P1A-specific TCR/IL-7/CCL19/eGFP-expressing T cells or the P1A-specific TCR/eGFP-expressing T cells (both the cells were 70 to 80% eGFP-positive) were intravenously administered at 1×10⁶ cells to each mouse. Then, the survival rate of each mouse was analyzed while the tumor volumes of dead mice were measured. The results of analyzing the survival rate of each mouse are shown in FIG. 7, and the results of measuring the tumor volumes of dead mice are shown in FIG. 8.

In FIG. 7, ▲ represents the results about untreated mice, ■ represents the results about the mice given the P1A-specific TCR/eGFP-expressing T cells, ● represents the results about the mice given the P1A-specific TCR/IL-7/CCL19/eGFP-expressing T cells, the abscissa represents the number of days (day) after subcutaneous inoculation of P815 mastocytoma, and the ordinate represents the survival rate (%). 80% of the mice given the P1A-specific TCR/IL-7/CCL19/eGFP-expressing T cells survived even on day 60, and 50% thereof survived even after 100 days. Thus, use of the immunocompetent cells expressing P1A-specific TCR, IL-7 and CCL19 was shown to exert an antitumor effect and suppress decrease in survival rate caused by tumor.

In FIG. 8, the abscissa represents the number of days (day) after subcutaneous inoculation of P815 mastocytoma, and the ordinate represents the tumor volume (mm³). As is evident from FIG. 8, increase in tumor volume was remarkably suppressed in the mice given the P1A-specific TCR/IL-7/CCL19/eGFP-expressing T cells, demonstrating that the P1A-specific TCR/IL-7/CCL19/eGFP-expressing T cells have excellent antitumor activity and exert a therapeutic effect on solid cancer.

INDUSTRIAL APPLICABILITY

The IL-7×CCL19-expressing immunocompetent cell of the present invention possesses all of proliferative potential, survival capacity and the ability to accumulate a lymphocyte and is therefore applicable in the field of immunotherapy.

The invention claimed is:

1. An isolated immunocompetent cell comprising (i) an exogenous nucleic acid encoding a T cell receptor specifically recognizing a cancer antigen bound with a major histocompatibility complex (MHC) molecule, (ii) an exogenous nucleic acid encoding interleukin 7 (IL-7), and (iii) an exogenous nucleic acid encoding CCL19.

2. The isolated immunocompetent cell according to claim 1, wherein the immunocompetent cell is a T cell.

3. The isolated immunocompetent cell according to claim 1, wherein the cancer antigen is WT1, MART-1, NY-ESO-1, MAGE-A1, MAGE-A3, MAGE-A4, Glypican-3, KIF20A, Survivin, AFP-1, gp100, MUC1, PAP-10, PAP-5, TRP2-1, SART-1, VEGFR1, VEGFR2, NEIL3, MPHOSPH1, DEPDC1, FOXM1, CDH3, TTK, TOMM34, URLC10, KOC1, UBE2T, TOPK, ECT2, MESOTHELIN, NKG2D, PIA, GD2, or GM2.

4. An anticancer agent comprising the isolated immunocompetent cell according to claim 1 and a pharmaceutically acceptable additive.

5. The isolated immunocompetent cell according to claim 3, wherein the immunocompetent cell is a T cell.

6. The isolated immunocompetent cell according to claim 1, wherein the isolated immunocompetent cell contains a recombinant nucleic acid molecule encoding said T cell receptor, said IL-7, and said CCL19.

7. The isolated immunocompetent cell according to claim 1, wherein the immunocompetent cell is a lymphoid cell, an antigen-presenting cell, or a granulocyte.

8. The isolated immunocompetent cell according to claim 1, wherein said T cell receptor consists of an alpha chain and a beta chain.

9. The isolated immunocompetent cell according to claim 1, wherein said T cell receptor consists of a gamma chain and a delta chain.

10. The isolated immunocompetent cell according to claim 1, comprising an expression vector (a) containing (i) the exogenous nucleic acid encoding a T cell receptor specifically recognizing a cancer antigen bound with an MHC molecule, (ii) the exogenous nucleic acid encoding IL-7, and (iii) the exogenous nucleic acid encoding CCL19.

11. The isolated immunocompetent cell according to claim 10, wherein (i) the exogenous nucleic acid encoding a T cell receptor specifically recognizing a cancer antigen bound with a MHC molecule, (ii) the exogenous nucleic acid encoding IL-7, and (iii) the exogenous nucleic acid encoding CCL19 in the expression vector (a) are linked via a sequence encoding a self-cleaving peptide.

12. The isolated immunocompetent cell according to claim 1, comprising
    an expression vector (b-1) containing (i) the exogenous nucleic acid encoding a T cell receptor specifically recognizing a cancer antigen bound with an MHC molecule; and
    an expression vector (b-2) containing (ii) the exogenous nucleic acid encoding IL-7, and (iii) the exogenous nucleic acid encoding CCL19.

13. The isolated immunocompetent cell according to claim 12, wherein (ii) the exogenous nucleic acid encoding IL-7, and (iii) the exogenous nucleic acid encoding CCL19 in the expression vector (b-2) are linked via a sequence encoding a self-cleaving peptide.

14. The isolated immunocompetent cell according to claim 1, comprising
    an expression vector (c-1) containing (i) the exogenous nucleic acid encoding a T cell receptor specifically recognizing a cancer antigen bound with an MHC molecule, and (ii) the exogenous nucleic acid encoding IL-7; and
    an expression vector (c-2) containing (iii) the exogenous nucleic acid encoding CCL19.

15. The isolated immunocompetent cell according to claim 14, wherein (i) the exogenous nucleic acid encoding a T cell receptor specifically recognizing a cancer antigen bound with an MHC molecule, and (ii) the exogenous nucleic acid encoding IL-7 in the expression vector (c-1) are linked via a sequence encoding a self-cleaving peptide.

16. The isolated immunocompetent cell according to claim 1, comprising
    an expression vector (d-1) containing (ii) the exogenous nucleic acid encoding IL-7; and
    an expression vector (d-2) containing (i) the exogenous nucleic acid encoding a T cell receptor specifically recognizing a cancer antigen bound with an MHC molecule, and (iii) the exogenous nucleic acid encoding CCL19.

17. The isolated immunocompetent cell according to claim 16, wherein (i) the exogenous nucleic acid encoding a T cell receptor specifically recognizing a cancer antigen bound with a MHC molecule, and (iii) the exogenous nucleic acid encoding CCL19 in the expression vector (d-2) are linked via a sequence encoding a self-cleaving peptide.

18. The isolated immunocompetent cell according to claim 1, comprising
    an expression vector (e-1) containing (i) the exogenous nucleic acid encoding a T cell receptor specifically recognizing a cancer antigen bound with an MHC molecule;
    an expression vector (e-2) containing (ii) the exogenous nucleic acid encoding IL-7; and
    an expression vector (e-3) containing (iii) the exogenous nucleic acid encoding CCL19.

19. The isolated immunocompetent cell according to claim 10, wherein the expression vector contains a nucleic acid encoding a suicide gene.

\* \* \* \* \*

(12) SUPPLEMENTAL EXAMINATION CERTIFICATE

United States Patent
Tamada et. al.

(10) Number: US 11,337,997 F1
(45) Certificate Issued: Oct. 27, 2022

Control No.: 96/000,412

Filing Date: Sep. 12, 2022

Primary Examiner: Sharon Turner

No substantial new question of patentability is raised in the request for supplemental examination. See the Reasons for Substantial New Question of Patentability Determination in the file of this proceeding.

(56) Items of Information

OTHER DOCUMENTS

Jones, B.S., et. al., Improving the Safety of Cell Therapy products by Suicide Gene Transfer, Frontiers in Pharmacology, Vol. 5, Art. 254, pp. 1-8, 27 Nov., 2014.

SEQUENCE LISTING

```
<160> NUMBER OF SEQ ID NOS: 14

<210> SEQ ID NO 1
<211> LENGTH: 177
<212> TYPE: PRT
<213> ORGANISM: artificial
<220> FEATURE:
<223> OTHER INFORMATION: human IL-7
<220> FEATURE:
<223> OTHER INFORMATION: Inventor: Tamada, Koji
      Inventor: Sakoda, Yukimi
      Inventor: Adachi, Keishi

<400> SEQUENCE: 1

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
```

```
                145                 150                 155                 160
Gln Glu Ile Lys Thr Cys Trp Asn Lys Ile Leu Met Gly Thr Lys Glu
                    165                 170                 175

His

<210> SEQ ID NO 2
<211> LENGTH: 98
<212> TYPE: PRT
<213> ORGANISM: artificial
<220> FEATURE:
<223> OTHER INFORMATION: human CCL19

<400> SEQUENCE: 2

Met Ala Leu Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
        35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser

<210> SEQ ID NO 3
<211> LENGTH: 22
<212> TYPE: DNA
<213> ORGANISM: artificial
<220> FEATURE:
<223> OTHER INFORMATION: 5'-R primer

<400> SEQUENCE: 3
gtctaccagg cattcgcttc at                                           22

<210> SEQ ID NO 4
<211> LENGTH: 24
<212> TYPE: DNA
<213> ORGANISM: artificial
<220> FEATURE:
<223> OTHER INFORMATION: 3-TRa-C primer

<400> SEQUENCE: 4
tcagctggac cacagccgca gcgt                                         24

<210> SEQ ID NO 5
<211> LENGTH: 21
<212> TYPE: DNA
<213> ORGANISM: artificial
<220> FEATURE:
<223> OTHER INFORMATION: 3-TRb-C1 primer

<400> SEQUENCE: 5
tcagaaatcc tttctcttga c                                            21

<210> SEQ ID NO 6
<211> LENGTH: 24
<212> TYPE: DNA
<213> ORGANISM: artificial
<220> FEATURE:
```

<223> OTHER INFORMATION: 3-TRbeta-C2 primer

<400> SEQUENCE: 6
ctagcctctg gaatcctttc tctt                                          24

<210> SEQ ID NO 7
<211> LENGTH: 8
<212> TYPE: PRT
<213> ORGANISM: artificial
<220> FEATURE:
<223> OTHER INFORMATION: 2A peptide cleavage region
<220> FEATURE:
<221> NAME/KEY: MISC_FEATURE
<222> LOCATION: (2)..(2)
<223> OTHER INFORMATION: Val or Ile
<220> FEATURE:
<221> NAME/KEY: MISC_FEATURE
<222> LOCATION: (4)..(4)
<223> OTHER INFORMATION: any amino acid

<400> SEQUENCE: 7

Asp Xaa Glu Xaa Asn Pro Gly Pro
1               5

<210> SEQ ID NO 8
<211> LENGTH: 25
<212> TYPE: PRT
<213> ORGANISM: artificial
<220> FEATURE:
<223> OTHER INFORMATION: 2Apeptide(F2A)

<400> SEQUENCE: 8

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 9
<211> LENGTH: 1674
<212> TYPE: DNA
<213> ORGANISM: artificial
<220> FEATURE:
<223> OTHER INFORMATION: anti-FITC CAR

<400> SEQUENCE: 9
atggagttgc ctgttaggtt gttggtgctg atgttctgga ttcctgcttc cagcagtgat      60
gtcgtgatga cccaaactcc actctccctg cctgtcagtc ttggagatca agcctccatc    120
tcttgcagat ctagtcagag ccttgtacac agtaatggaa acacctattt acgttggtac    180
ctgcagaagc caggccagtc tccaaaggtc ctgatctaca agtttccaa ccgattttct     240 ggggtcccag acaggttcag tggcagtgga tcagggacag atttcacact caagatcagc    300
agagtggagg ctgaggatct gggagtttat ttctgctctc aaagtacaca tgttccgtgg    360
acgttcggtg aggcaccaa gctggaaatc aaaagtagtg ctgatgatgc taagaaggat    420
gctgctaaga aggatgatgc taagaaggat gatgctaaga aggatggtga ggtgaagctg    480
gatgagactg gaggaggctt ggtgcaacct gggaggccca tgaaactctc ctgtgttgcc    540
tctggattca cttttagtga ctactggatg aactgggtcc gccagtctcc agagaaagga    600
ctggagtggg tagcacaaat tagaaacaaa ccttataatt atgaaacata ttattcagat    660
tctgtgaaag gcagattcac catctcaaga gatgattcca aaagtagtgt ctacctgcaa    720
atgaacaact taagagttga agacatgggt atctattact gtacgggttc ttactatggt    780

```
atggactact ggggtcaagg aacctcagtc accgtctccg cggccgcagt cgtgccagtc    840
cttcagaaag tgaactctac tactaccaag ccagtgctgc gaactccctc acctgtgcac    900
cctaccggga catctcagcc ccagagacca agaagattgtc ggccccgtgg ctcagtgaag    960
gggaccggat tggacttcgc ctgtgatatt tacatctggg caccctttggc cggaatctgc   1020 gtggcccctc tgctgtcctt gatcatcact ctcatctgct accacaggag ccgaaatagt   1080
agaaggaaca gactccttca aagtgactac atgaacatga ctccccggag gcctgggctc   1140
actcgaaagc cttaccagcc ctacgcccct gccagagact ttgcagcgta ccgccccaaa   1200
tggatcagga aaaaattccc ccacatattc aagcaaccat ttaagaagac cactggagca   1260
gctcaagagg aagatgcttg tagctgccga tgtccacagg aagaagaagg aggaggagga   1320
ggctatgagc tgagagcaaa attcagcagg agtgcagaga ctgctgccaa cctgcaggac   1380
cccaaccagc tctacaatga gctcaatcta gggcgaagag aggaatatga cgtcttggag   1440
aagaagcggg ctcgggatcc agagatggga ggcaaacagc agaggaggag gaacccccag   1500
gaaggcgtat acaatgcact gcagaaagac aagatggcag aagcctacag tgagatcggc   1560
acaaaaggcg agaggcggag aggcaagggg cacgatggcc tttaccaggg tctcagcact   1620
gccaccaagg acacctatga tgccctgcat atgcagaccc tggcccctcg ctaa          1674
```

<210> SEQ ID NO 10
<211> LENGTH: 146
<212> TYPE: DNA
<213> ORGANISM: artificial
<220> FEATURE:
<223> OTHER INFORMATION: F2A-MCS

<400> SEQUENCE: 10

```
ggaagcggag tgaaacagac tttgaatttt gaccttctca agttggcggg agacgtggag     60
tccaaccctg gaccatgcat aaaaagctta aaccagttaa ctggaaaacg cgtaaagtcg    120
acaaaggcca aaaaggccaa cgtacg                                         146
```

<210> SEQ ID NO 11
<211> LENGTH: 864
<212> TYPE: DNA
<213> ORGANISM: artificial
<220> FEATURE:
<223> OTHER INFORMATION: mouseIL-7-F2A-mouseCCL19

<400> SEQUENCE: 11

```
atgttccatg tttcttttag atatatcttt ggaattcctc cactgatcct tgttctgctg     60
cctgtcacat catctgagtg ccacattaaa gacaaagaag gtaaagcata tgagagtgta    120
ctgatgatca gcatcgatga attggacaaa atgacaggaa ctgatagtaa ttgcccgaat    180
aatgaaccaa acttttttag aaaacatgta tgtgatgata caaaggaagc tgcttttcta    240
aatcgtgctg ctcgcaagtt gaagcaattt cttaaaatga atatcagtga agaattcaat    300
gtccacttac taacagtatc acaaggcaca caaacactgg tgaactgcac aagtaaggaa    360
gaaaaaaacg taaggaaca gaaaagaat gacgcatgtt tcctaaagag actactgaga    420
gaaataaaaa cttgttggaa taaaattttg aagggcagta taggaagcgg agtgaaacag    480
actttgaatt ttgaccttct caagttggcg ggagacgtgg agtccaaccc tggacctatg    540 gcccccgtg tgaccccact cctggccttc agcctgctgg ttctctggac cttcccagcc    600
ccaactctgg ggggtgctaa tgatgcgaa gactgctgcc tgtctgtgac ccagcgcccc    660
atccctggga acatcgtgaa agccttccgc taccttctta atgaagatgg ctgcagggtg    720
```

| | |
|---|---|
| cctgctgttg tgttcaccac actaaggggc tatcagctct gtgcacctcc agaccagccc | 780 |
| tgggtggatc gcatcatccg aagactgaag aagtcttctg ccaagaacaa aggcaacagc | 840 |
| accagaagga gccctgtgtc ttga | 864 |

<210> SEQ ID NO 12
<211> LENGTH: 783
<212> TYPE: DNA
<213> ORGANISM: artificial
<220> FEATURE:
<223> OTHER INFORMATION: anti-humanCD20 scFv

<400> SEQUENCE: 12

| | |
|---|---|
| atggactgga cctggcggat cctgttcctg gtggctgctg ctacaggcgc ccacagccag | 60 |
| atcgtgctgt ctcagtctcc cgccatcctg tctgctagcc ctggcgagaa agtgaccatg | 120 |
| acctgcagag ccagcagcag cgtgtcctac atccactggt tccagcagaa gcccggcagc | 180 |
| agccccaagc cttggatcta cgccacaagc aacctggcct ctggcgtgcc agtgcggttt | 240 |
| agcggctctg gctctggcac cagctacagc ctgaccatca gcagagtgga agccgaggac | 300 |
| gccgccacct actactgtca gcagtggacc agcaaccccc ccacattcgg cggaggcacc | 360 |
| aagctggaaa tcaagggcgg aggcggatct ggcggcggag gatctggggg aggcggctct | 420 |
| caggtgcagc tgcagcagcc tggcgctgag ctcgtgaaac tggcgcctc cgtgaagatg | 480 |
| agctgcaagg ccagcggcta caccttcaca agctacaaca tgcactgggt caagcagacc | 540 |
| cctggcagag gcctggaatg gatcggcgct atctacccccg gcaacggcga cacctcctac | 600 |
| aaccagaagt tcaagggcaa ggccaccctg accgccgaca gagcagcag cacagcctac | 660 |
| atgcagctgt cctccctgac cagcgaggac agcgccgtgt actactgcgc cagatctacc | 720 |
| tactacggcg gcgactggta cttcaacgtg tggggcgctg gcaccaccgt gaccgtgtct | 780 |
| gct | 783 |

<210> SEQ ID NO 13
<211> LENGTH: 1665
<212> TYPE: DNA
<213> ORGANISM: artificial
<220> FEATURE:
<223> OTHER INFORMATION: Mouse Il-7-F2A-mouseCCL19-F2A-eGFP

<400> SEQUENCE: 13

| | |
|---|---|
| atggtccacg tctccttcag atacatcttc ggcatccccc ccctgatcct ggtcctcctg | 60 |
| cctgtcacct ccagcgaatg tcatatcaag gacaaagagg gcaaggctta tgagagcgtc | 120 |
| ctgatgatct ccattgatga gctggataag atgaccggca ccgacagcaa ctgtcccaac | 180 |
| aatgagccca acttctttag aaagcacgtg tgtgacgata ccaaggaggc tgccttcctg | 240 |
| aacagggccg ccagaaagct gaagcagttc ctgaagatga catttccga ggagttcaac | 300 |
| gtgcacctcc tcaccgtgag ccagggcacc cagacactgg tcaattgcac tccaaggag | 360 |
| gagaagaacg tgaaagagca gaaaaagaat gatgcttgtt tcctcaagag gctgctgagg | 420 |
| gagatcaaga cctgttggaa taagatcctg aaaggcagca tcggcagcgg agtcaagcaa | 480 |
| accctgaact tcgacctgct gaaactggcc ggagatgtgg agagcaatcc cggccctatg | 540 |
| gccccccagag tcacccctct gctggccttc agcctgctcg tgctgtggac cttccccgct | 600 |
| cccacccctgg gcggcgccaa tgatgctgag gactgttgcc tctccgtgac ccagaggccc | 660 |
| atccctggaa acatcgtcaa agccttcagg tacctgctca acgaagacgg atgtagggtg | 720 |

```
cctgccgtgg tgttcacaac actgagaggc taccagctct gcgcccctcc tgatcagccc    780
tgggtcgaca gaatcatcag aaggctgaag aagtccagcg ccaagaacaa aggcaatagc    840
acaaggagaa gccctgtgag cgaattcgga agcggagtga aacagacttt gaattttgac    900
cttctcaagt tggcgggaga cgtggagtcc aaccctggac catgcatggt gagcaagggc    960
gaggagctgt tcaccggggt ggtgcccatc ctggtcgagc tggacggcga cgtaaacggc   1020
cacaagttca gcgtgtccgg cgagggcgag ggcgatgcca cctacggcaa gctgaccctg   1080
aagttcatct gcaccaccgg caagctgccc gtgccctggc ccaccctcgt gaccaccctg   1140
acctacggcg tgcagtgctt cagccgctac cccgaccaca tgaagcagca cgacttcttc   1200
aagtccgcca tgcccgaagg ctacgtccag gagcgcacca tcttcttcaa ggacgacggc   1260
aactacaaga cccgcgccga ggtgaagttc gagggcgaca ccctggtgaa ccgcatcgag   1320
ctgaagggca tcgacttcaa ggaggacggc aacatcctgg gcacaagct ggagtacaac   1380 tacaacagcc acaacgtcta tatcatggcc gacaagcaga agaacggcat caaggtgaac   1440
ttcaagatcc gccacaacat cgaggacggc agcgtgcagc tcgccgacca ctaccagcag   1500 aacacccca tcggcgacgg ccccgtgctg ctgcccgaca accactacct gagcacccag   1560
tccgccctga gcaaagaccc caacgagaag cgcgatcaca tggtcctgct ggagttcgtg   1620
accgccgccg ggatcactct cggcatggac gagctgtaca agtaa             1665
```

<210> SEQ ID NO 14
<211> LENGTH: 554
<212> TYPE: PRT
<213> ORGANISM: artificial
<220> FEATURE:
<223> OTHER INFORMATION: Mouse Il-7-F2A-mouse CCL19-2A-eGFP amino acid

<400> SEQUENCE: 14

```
Met Val His Val Ser Phe Arg Tyr Ile Phe Gly Ile Pro Pro Leu Ile
1               5                   10                  15

Leu Val Leu Leu Pro Val Thr Ser Ser Glu Cys His Ile Lys Asp Lys
            20                  25                  30

Glu Gly Lys Ala Tyr Glu Ser Val Leu Met Ile Ser Ile Asp Glu Leu
        35                  40                  45

Asp Lys Met Thr Gly Thr Asp Ser Asn Cys Pro Asn Asn Glu Pro Asn
    50                  55                  60

Phe Phe Arg Lys His Val Cys Asp Asp Thr Lys Glu Ala Ala Phe Leu
65                  70                  75                  80

Asn Arg Ala Ala Arg Lys Leu Lys Gln Phe Leu Lys Met Asn Ile Ser
                85                  90                  95

Glu Glu Phe Asn Val His Leu Leu Thr Val Ser Gln Gly Thr Gln Thr
            100                 105                 110

Leu Val Asn Cys Thr Ser Lys Glu Glu Lys Asn Val Lys Glu Gln Lys
        115                 120                 125

Lys Asn Asp Ala Cys Phe Leu Lys Arg Leu Leu Arg Glu Ile Lys Thr
    130                 135                 140

Cys Trp Asn Lys Ile Leu Lys Gly Ser Ile Gly Ser Gly Val Lys Gln
145                 150                 155                 160

Thr Leu Asn Phe Asp Leu Leu Lys Leu Ala Gly Asp Val Glu Ser Asn
                165                 170                 175

Pro Gly Pro Met Ala Pro Arg Val Thr Pro Leu Leu Ala Phe Ser Leu
            180                 185                 190

Leu Val Leu Trp Thr Phe Pro Ala Pro Thr Leu Gly Gly Ala Asn Asp
```

-continued

```
                195                 200                 205
Ala Glu Asp Cys Cys Leu Ser Val Thr Gln Arg Pro Ile Pro Gly Asn
    210                 215                 220
Ile Val Lys Ala Phe Arg Tyr Leu Leu Asn Glu Asp Gly Cys Arg Val
225                 230                 235                 240
Pro Ala Val Val Phe Thr Thr Leu Arg Gly Tyr Gln Leu Cys Ala Pro
                245                 250                 255
Pro Asp Gln Pro Trp Val Asp Arg Ile Ile Arg Arg Leu Lys Lys Ser
                260                 265                 270
Ser Ala Lys Asn Lys Gly Asn Ser Thr Arg Arg Ser Pro Val Ser Glu
            275                 280                 285
Phe Gly Ser Gly Val Lys Gln Thr Leu Asn Phe Asp Leu Leu Lys Leu
        290                 295                 300
Ala Gly Asp Val Glu Ser Asn Pro Gly Pro Cys Met Val Ser Lys Gly
305                 310                 315                 320
Glu Glu Leu Phe Thr Gly Val Val Pro Ile Leu Val Glu Leu Asp Gly
                325                 330                 335
Asp Val Asn Gly His Lys Phe Ser Val Ser Gly Glu Gly Glu Gly Asp
                340                 345                 350
Ala Thr Tyr Gly Lys Leu Thr Leu Lys Phe Ile Cys Thr Thr Gly Lys
            355                 360                 365
Leu Pro Val Pro Trp Pro Thr Leu Val Thr Thr Leu Thr Tyr Gly Val
        370                 375                 380
Gln Cys Phe Ser Arg Tyr Pro Asp His Met Lys Gln His Asp Phe Phe
385                 390                 395                 400
Lys Ser Ala Met Pro Glu Gly Tyr Val Gln Glu Arg Thr Ile Phe Phe
                405                 410                 415
Lys Asp Asp Gly Asn Tyr Lys Thr Arg Ala Glu Val Lys Phe Glu Gly
                420                 425                 430
Asp Thr Leu Val Asn Arg Ile Glu Leu Lys Gly Ile Asp Phe Lys Glu
            435                 440                 445
Asp Gly Asn Ile Leu Gly His Lys Leu Glu Tyr Asn Tyr Asn Ser His
        450                 455                 460
Asn Val Tyr Ile Met Ala Asp Lys Gln Lys Asn Gly Ile Lys Val Asn
465                 470                 475                 480
Phe Lys Ile Arg His Asn Ile Glu Asp Gly Ser Val Gln Leu Ala Asp
                485                 490                 495
His Tyr Gln Gln Asn Thr Pro Ile Gly Asp Gly Pro Val Leu Leu Pro
                500                 505                 510
Asp Asn His Tyr Leu Ser Thr Gln Ser Ala Leu Ser Lys Asp Pro Asn
            515                 520                 525
Glu Lys Arg Asp His Met Val Leu Leu Glu Phe Val Thr Ala Ala Gly
        530                 535                 540
Ile Thr Leu Gly Met Asp Glu Leu Tyr Lys
545                 550
```